US008945551B2

(12) United States Patent
Mainwaring et al.

(10) Patent No.: US 8,945,551 B2
(45) Date of Patent: Feb. 3, 2015

(54) BIOPOLYMER HYBRID GEL-DEPOT DELIVERY SYSTEM

(75) Inventors: David Edward Mainwaring, North Melbourne (AU); Mohammad Al Kobaisi, Glen Iris (AU); Brendon Yew Loong Chua, Mount Waverley (AU); David Charles Jackson, North Balwyn (AU)

(73) Assignee: Polymers CRC Ltd. (AU)

( * ) Notice: Subject to any disclaimer, the term of this patent is extended or adjusted under 35 U.S.C. 154(b) by 0 days.

(21) Appl. No.: 13/382,655

(22) PCT Filed: Jul. 9, 2010

(86) PCT No.: PCT/AU2010/000883
§ 371 (c)(1),
(2), (4) Date: Jun. 19, 2012

(87) PCT Pub. No.: WO2011/003155
PCT Pub. Date: Jan. 13, 2011

(65) Prior Publication Data
US 2012/0251536 A1    Oct. 4, 2012

(30) Foreign Application Priority Data
Jul. 9, 2009   (AU) .............................. 2009903213

(51) Int. Cl.
*A61K 39/395*     (2006.01)
*A61K 38/22*      (2006.01)
(Continued)

(52) U.S. Cl.
CPC ............... *A61K 9/0024* (2013.01); *A61K 47/02* (2013.01); *A61K 47/36* (2013.01)
USPC .................. 424/134.1; 424/133.1; 424/142.1; 514/5.9; 514/9.7; 514/11.3; 514/178; 514/179

(58) Field of Classification Search
CPC ...... A61K 9/0024; A61K 38/00; A61K 47/36; A61K 47/48784; A61K 9/122; A61K 8/24; A61K 47/02
See application file for complete search history.

(56) References Cited

U.S. PATENT DOCUMENTS 6,703,038 B1     3/2004  Schaefer et al.
2005/0084533 A1*  4/2005  Howdle et al. ................ 424/486
(Continued)

FOREIGN PATENT DOCUMENTS

EP    1774971 A1    4/2007
EP    1977739 A1   10/2008
(Continued)

OTHER PUBLICATIONS

Malhotra et al. Ultrafine chitosan nanoparticles as an efficient nucleic acid delivery system targeting neuronal cells. Drug Dev Ind Pharm. Jun. 2009; 35(6):719-26.*
(Continued)

*Primary Examiner* — Karlheinz R Skowronek
*Assistant Examiner* — Jia-Hai Lee
(74) *Attorney, Agent, or Firm* — Lathrop & Gage LLP; Brian C. Trinque; Teofilo Javier

(57) ABSTRACT

The invention relates to biopolymer-gel based depot systems for prolonged and/or controlled release delivery of biologically active agents, methods for the manufacture of the biopolymer based gel-depots which include a biologically active agent, and uses of such biopolymer gel-depots in therapy. The biopolymer-gel based depot systems comprise a biocompatible polyaminosaccharide and/or protein; a biocompatible phosphate and/or sulphonamide compound; a biologically active agent; an aqueous insoluble alkaline earth metal phosphate; and a biocompatible glycan and/or proteoglycan.

24 Claims, 33 Drawing Sheets

(51) Int. Cl.

| | |
|---|---|
| *A61K 38/27* | (2006.01) |
| *A61K 38/28* | (2006.01) |
| *A61K 31/566* | (2006.01) |
| *A61K 31/573* | (2006.01) |
| *A61K 9/00* | (2006.01) |
| *A61K 47/02* | (2006.01) |
| *A61K 47/36* | (2006.01) |

(56) References Cited

U.S. PATENT DOCUMENTS

2009/0010983 A1* 1/2009 Melvik et al. ............... 424/422
2009/0011008 A1   1/2009 Sung et al.

FOREIGN PATENT DOCUMENTS

| WO | 0249501 A2 | 6/2002 |
| WO | 2007087350 A2 | 8/2007 |
| WO | WO 2008/130529 A1 | 10/2008 |

OTHER PUBLICATIONS

Yin et al. Preparation and characterization of hydroxyapatite/chitosan—gelatin network composite. J. Appl. Polym. Sci. 2000; 77: 2929-2938.*

Vódná L. et al., "Chitosan Based Hydrogel Microspheres as Drug Carriers", Macromolecular Bioscience, 2007. vol. 7, No. 5, pp. 629-634.

International Search Report & Written Opinion from PCT/AU2010/000883, dated Aug. 23, 2010.

* cited by examiner (A)        (B)

BIOPOLYMER HYBRID GEL-DEPOT DELIVERY SYSTEM

RELATED APPLICATIONS

This application is a 35 U.S.C. §371 filing of International Patent Application No: PCT/AU2010/000883 which was filed on Jul. 9, 2010, and which claims priority to Australian Patent Application No: 2009903213, which was filed on Jul. 9, 2009. The entire contents of the aforementioned applications are hereby incorporated herein by reference.

FIELD OF INVENTION

The present invention generally relates to biopolymer-gel based systems for delivery of biological active agents. In particular, the present invention relates to biopolymer gel-depot delivery systems which provide prolonged and controlled delivery of biological active agents, methods for the manufacture of the biopolymer based gel-depots which include a biological active agent, and uses of such biopolymer gel-depots in therapy.

BACKGROUND OF INVENTION

Delivery systems which act as a vehicle to deliver an active agent in vivo are known and are designed primarily to a specific biomedical application. Some systems not only merely act by just carrying the active agent but are specifically designed to deliver the active in a more efficient manner. For instance, when such systems are designed there is particular emphasis on parameters such as mode of delivery (e.g., oral, topical, transmucosal, etc.), drug release profile, as well as ADME properties (Adsorption, Distribution, Metabolism and Excretion) of the drug in vivo.

Many biological active agents such as peptide/proteins, antibodies, vaccines and gene based therapeutics may not be effectively delivered using, for instance, the oral and transmucosal routes. Such therapeutics are often quite susceptible to enzymatic degradation or are insufficiently absorbed into the systemic circulation due to molecular size and/or charge. As such, many of these therapeutics are delivered by injection. For instance, many vaccines are based on the delivery of protein based drugs intravenously.

Also, typically, the administration of a biological active agent to a subject requires repeated administration of the active over a period of time in order for the active to provide the required effect. For example, immunization through the short term vaccination process has logistical and commercial disadvantages because it requires multiple vaccinations, boosters and high doses of vaccine generally, which result in increased cost to both industry and the end-users.

To date, vaccines are often delivered to a subject in the form of a dispersion (which can be solid or emulsion or liquid/liquid dispersions) or in particulate form, including microparticles, emulsions, immune stimulating complexes, liposomes, virosomes and virus-like particles.

However, despite the success of methods of initiating an immune response to an antigen they still require the antigen to be administered repeatedly to a subject. A similar problem occurs in the administration of numerous other drugs to subjects.

Accordingly, a need has evolved to develop drug-delivery systems for prolonged and better control in drug administration. The present invention seeks to address at least some of the shortcomings of the known delivery systems.

SUMMARY OF INVENTION

The present invention provides a biopolymer hybrid gel-depot including a biological active agent, which can be used to deliver a biological active agent to a subject in vivo. The biopolymer hybrid gel-depot of the present invention controls the rate of delivery of the agent to the subject thereby reducing the need for repeated administration of the agent. The biopolymer based system disclosed herein is capable of being injected, for instance, subcutaneously, forming a biopolymer hybrid gel-depot by rapid (spontaneous) crosslinking in vivo, without the need for separate curing mechanisms such as the application of UV and IR (including NIR) light, heat, or catalysts.

In one aspect the invention provides a prolonged release and/or controlled release delivery system for delivery of a biologically active agent, the system comprising:
(i) a first component comprising a biocompatible polyaminosaccharide and/or protein; and
(ii) a second component comprising a biocompatible phosphate and/or sulphonamide compound capable of crosslinking with the first component,
wherein
(a) the first and/or second component further comprises the biologically active agent; and
(b) the first and/or second component also comprises:
(i) an aqueous insoluble alkaline earth metal phosphate; and/or
(ii) a biocompatible glycan and/or proteoglycan; and
whereby the first and second components of the system are physically isolated and, when in use, combining of the first and second components promotes crosslinking and results in the formation of a biopolymer hybrid gel-depot including the biological active agent.

In a second aspect the invention provides a method of forming a prolonged release and/or controlled release biopolymer hybrid gel-depot including a biologically active agent, said method comprising:
(i) providing a first component comprising a biocompatible polyaminosaccharide and/or protein, and a second component comprising a biocompatible phosphate and/or sulphonamide compound capable of crosslinking with the first component,
(a) wherein the first and/or second component further comprises the biologically active agent; and
(b) wherein the first and/or second component also comprises:
(i) an aqueous insoluble alkaline earth metal phosphate; and/or
(ii) a biocompatible glycan and/or proteoglycan; and
(ii) combining the first and second components for a time and under conditions to promote crosslinking and to form a biopolymer hybrid gel-depot including the biologically active agent.

DETAILED DESCRIPTION OF THE INVENTION

Figure 1:
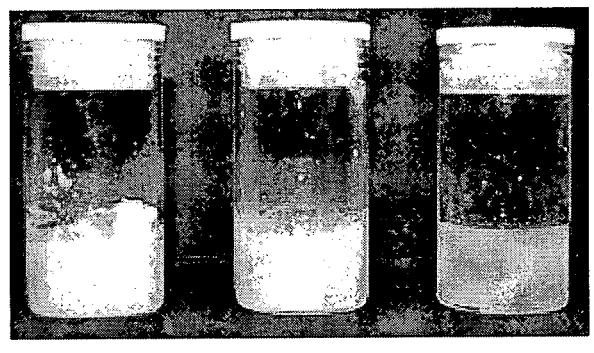
FIG. 1 A photographic image of the products of the chitosan gelation (reference example 1) using 26 wt % Hydroxyapatite in 0.001 M phosphate buffer, pH 6.8; (A) 75 wt %, (B) 50 wt %, and (C) 25 wt % hydroxyapatite:chitosan.

The present invention is predicated (in part) on the elucidation that combining a biocompatible polyaminosaccharide and/or protein ('first component') with a biocompatible phosphate and/or sulphonamide compound capable of crosslinking with the first component ('second component') results in rapid (spontaneous) cross-linking and subsequent biopolymer hybrid gel-depot formation and that this can occur spontaneously in vivo after injection.

The aforementioned first and second components are thought to form the biopolymer hybrid gel-depot by spontaneous crosslinking, gelation and phase separation mechanisms. Biopolymer hybrid gel formation is thought to occur without significant volume change and thus has an unchanged initial aqueous phase composition. Upon phase separation, the gel phase would then undergo shrinkage, driven by further crosslinking and osmotic pressure resulting in exclusion of the aqueous phase (syneresis), until the rate of growth of the gel density is counterbalanced by the elastic forces of the crosslinked network. The result of such processes (gelation and phase separation, further crosslinking and synersis) leads to the spontaneous formation of a compressed compliant biopolymer hybrid gel-depot with the exclusion of a clear excess non-swelling aqueous phase.

The biopolymer hybrid gel-depot of the present invention is biocompatible and has metabolites/degradation products that are biocompatible. Biocompatibility is a concept known to those in the art. It is a relative rather than an absolute term, in that most exogenous substances illicit some form of immune response and are thus not absolutely biocompatible. Biocompatible exogenous substances are those that illicit acceptable immune responses. Accordingly, as used herein the term "biocompatible" refers to a component that is biologically compatible such that it substantially does not elicit an adverse immune, toxic or injurious response in vivo, or adversely integrates with a particular cell type or tissue.

The First Component

The first component comprises any suitable biocompatible polyaminosaccharide and/or protein.

In particular, the biocompatible polyaminosaccharide and/or protein may be selected from suitable polyaminosaccharides such as chitosan, chitin and hyaluronan (as well as salts), and suitably functionalised derivatives thereof.

In one embodiment the first component comprises a biocompatible protein such as albumin and collagen (or suitable salts), or suitably functionalised derivatives thereof.

In another embodiment, the first component comprises a biocompatible polyaminosaccharide selected from chitosan, salts thereof, or suitably functionalised derivatives thereof.

In another embodiment, the first component comprises: (i) a mixture of polyaminosaccharides, (ii) a mixture of proteins, or (iii) a mixture of polyaminosaccharides and proteins.

It would be appreciated that as the first component must be capable of crosslinking with the biocompatible phosphate and/or sulphonamide of the second component, a suitable biocompatible polyaminosaccharide and/or protein of the first component is one which is characterised with a chemical moiety bearing a functionality capable of crosslinking. In this regard, preferably the biocompatible polyaminosaccharide and/or protein is selected from those which bear an electrophilic group capable of crosslinking with the second component under physiological conditions. Preferred electrophilic groups include ammonium, alkyl ammonium and electrophilic derivatives thereof. More preferably the electrophilic group is alkylammonium and more preferably —$CH_2$—$NH_3^+$. As such suitable functionality on a biocompatible polyaminosaccharide and/or protein includes amine and alkylamine groups which can be protonated and remain so under physiological conditions. In a preferred embodiment the first component comprises chitosan, a salt thereof, or a suitable functional derivative thereof, which maintains the ability to crosslink with the second component under physiological conditions. In an embodiment, the first component may also be pH buffered to ensure that the amino groups are protonated and capable of crosslinking with the second component. For instance, when the first component comprises chitosan it is preferred that the first component is in the form of an acidic aqueous solution. This may be achieved by dissolving chitosan in an acidic aqueous solution, such as, for instance, a 1% acetic acid solution.

Chitosan is a linear polyaminosaccharide composed of randomly distributed β-(1-4)-linked D-glucosamine (a deacetylated unit) and N-acetyl-D-glucosamine (an acetylated unit). The degree of deacetylation (% DA) can be determined by NMR spectroscopy, and the % DA in commercial chitosan is in the range 60-100%.

Chitosan is biocompatible, enzymatically biodegradable (for example by lysozyme hydrolysis), and non-toxic (its degradation products are relatively non-immunogenic and non-carcinogenic).

The amino group in chitosan has a pKa value of ~6.5. Thus, chitosan is positively charged (i.e. the amino groups are protonated) and soluble in acidic to neutral solution with a charge density dependent on pH and the % DA-value. In other words, chitosan can act as a positively charged polyelectrolyte under physiological conditions and thus has appropriate functionality to be crosslinked with the second component.

The molecular weight of chitosan can also be modified to affect its properties. As long as the modification does not adversely affect the resulting derivative's ability to crosslink, then such derivatives are also contemplated and are encompassed herein by the term "suitably functionalised derivatives".

In an embodiment, the chitosan is a short chain chitosan of a molecular weight (Mw) of between 40-150 kDa. More preferably the Mw is in the range of 50-100 kDa and even more preferably 50-80 kDa.

The Second Component

The second component comprises a phosphate and/or sulphonamide compound capable of crosslinking with the first component. Accordingly, the phosphate and/or sulphonamide compound can be selected from those suitably functionalised as to promote crosslinking between the biocompatible polyaminosaccharide and/or protein of the first component. The second component is preferably selected from phosphate and/or sulphonamide components which facilitate rapid (spontaneous) crosslinking and gel-depot formation in vivo. Suitable crosslinking phosphate compounds include tripolyphosphate, and salts thereof. Commonly known salts of tripolyphosphate include sodium tripolyphosphate and potassium tripolyphosphate. Sodium tripolyphosphate (STPP, sometimes STP or sodium triphosphate or TPP), with formula $Na_5P_3O_{10}$, is a polyphosphate of sodium. It is the sodium salt of triphosphoric acid.

Suitable other crosslinking sulphonamide components include (bis)sulphosuccinimidyl suberate, and diaminocarboxysulphonate.

Other suitable crosslinking compounds include glutaraldehyde and epichlorohydrin.

In an embodiment, the second component comprises (i) a phosphate crosslinker (or mixture thereof), (ii) a sulphonamide crosslinker (or mixture thereof), or (iii) a mixture of phosphate and sulphonamide crosslinkers.

In a preferred embodiment, the second component comprises TPP.

In a further embodiment, the second component may comprise an additional compound which further promotes the crosslinking of the first and second components. Such crosslinking promoters include, for instance, the use of an acidic medium to protonate alkylamine groups on the biocompatible polyaminosaccharide and/or protein as discussed previously in relation to chitosan.

In another embodiment the biocompatible polyaminosaccharide and/or protein ('first component') and the biocompatible phosphate and/or sulphonamide are present in the system in a wt/wt ratio range of about 1:1-1:2.

The first and/or second components of the delivery system further comprises a biocompatible aqueous insoluble alkaline earth metal phosphate, and/or a biocompatible glycan and/or proteoglycan which is characterised with multiple negative charges at physiological pH, in addition to the biologically active agent.

The Aqueous Insoluble Alkaline Earth Metal Phosphate

These include all suitable aqueous insoluble phosphates of calcium and magnesium which are able to provide rigidity to the structure of cell walls of the resultant gel-depot (i.e., bone likeness"). Doped calcium phosphate, such as $Mg^{2+}$, $Zn^{2+}$, $Na^+$, $CO^{2-}$ and $SiO_4^{4-}$ doped calcium phosphates may also be used.

In one embodiment the aqueous insoluble alkaline earth metal phosphate is apatite.

Apatite is a group of phosphate minerals and includes fluorapatite, $Ca_5(PO_4)F_3$; chlorapatite, $Ca_5(PO_4)_3Cl$; bromapatite $Ca_5(PO_4)_3Br$ and hydroxyapatite, $Ca_5(PO_4)_3(OH)$ (which are also often usually written $Ca_{10}(PO_4)_6(OH, F, Cl, Br)_2$ to denote that the crystal unit cell comprises two molecules). Hydroxyapatite crystallizes in the hexagonal crystal system. It has a specific gravity of 3.1-3.2 and has a hardness of 5 on the Mohs hardness scale. Hydroxyapatite can be found in teeth (enamel) and bones. About 70% of bone is comprised of hydroxyapatite.

In a preferred embodiment the aqueous insoluble alkaline earth metal phosphate is hydroxyapatite.

In an embodiment, the aqueous insoluble alkaline earth metal phosphate is present in the first component. In this embodiment it is preferred that the wt/wt ratio range of aqueous insoluble alkaline earth metal phosphate: polyaminosaccharide and/or protein of the first component is about 1:6-1:12. In a further preferred embodiment wherein the aqueous insoluble alkaline earth metal phosphate is hydroxyapatite and the polyaminosaccharide and/or protein is chitosan the preferred wt/wt ratio of the hydroxyapatite:chitosan is about 1:1-1:4 and more preferably the wt/wt ratio is 1:1.

In another embodiment, the aqueous insoluble alkaline earth metal phosphate is present in the second component. In this embodiment it is preferred that the wt/wt ratio range of aqueous insoluble alkaline earth metal phosphate (e.g., hydroxyapatite): biocompatible phosphate and/or sulphonamide (e.g., TTP) is 1:6-1:12.

The Biocompatible Glycan and/or Proteoglycan

While the characteristics of the aforementioned aqueous soluble alkaline earth metal phosphate affords to the structure of the gel-depot defined rigidity, the "bone likeness" provided by the phosphate does have a disadvantage. The present inventors have also found that rigid bone-like gel-depots may also lead to granuloma formation, which is undesirable for subcutaneous delivery systems.

In order to overcome this problem and without wanting to be bound by any particular theory, the inventors have also found that the addition of biocompatible proteoglycans and/or glycans allows the gel-depot to be more pliable, providing plastic like properties to the gel-depot while retaining structure and therefore minimising any adverse immunological or injurious response. It is thought that the addition of proteoglycans and/or glycans may prevent crystallisation and growth of the alkaline earth metal phosphate which, alone, would cause the gel-depot to become too rigid and granular leading to tissue irritation and lower bio-erosion. Accordingly, another advantage from the addition of the proteoglycan and/or glycans is observed in longer term stability in addition to the gel-depot structure retaining its compliance.

Accordingly, in an embodiment either the first and/or second component the system and method according to the present invention includes at least one proteoglycan, glycan or a mixture thereof, which is preferably characterised with multiple negative charges at physiological pH.

A suitable glycan includes carboxymethyl cellulose (CMC).

Proteoglycans are glycoproteins that are heavily glycosylated. Suitable proteoglycans include: chondroitin, hyaluronate dextran, pentosan, keratan, dermatan and heparan (and derivatives thereof such as chondroitin sulphate, sodium hyaluronate, dermatan sulphate, and heparan sulfate), heparin (and derivatives thereof), aggrecan (and derivatives thereof).

In a preferred embodiment the biocompatible glycan and/or proteoglycan which is characterised with multiple negative charges at physiological pH is a proteoglycan or mixture thereof.

In a preferred embodiment the proteoglycan component is chondroitin sulphate. Chondroitin sulphate is a sulphated glycosaminoglycan composed of an unbranched polysaccharide chain of alternating sugars (N-acetyl-galactosamine and glucuronic acid). The sulphate is covalently attached to the sugar. If some glucuronic acid residues are epimerized into L-iduronic acid, the resulting disaccharide is then referred to as dermatan sulphate. Since the molecule has multiple negative charges at physiological pH, a cation is present in salts of chondroitin sulphate. Commercial preparations of chondroitin sulphate typically are the sodium salt. In this regard in a selection of an appropriate proteoglycan to be employed in the depots of the present invention any proteoglycan derivative which exhibits the same multiple negative charges (at physiological pH) would also be suitable.

Chondroitin sulphate is a major component of the extracellular matrix, and is important in maintaining the structural integrity of the tissue. It is also an important structural component of cartilage, as part of aggrecan, and provides much of its resistance to compression through the tightly packed and highly charged sulphate groups of chondroitin sulphate.

A chondroitin chain can have over 100 individual sugars, each of which can be sulphated in variable positions and quantities. Each monosaccharide may be left unsulphated, sulphated once, or sulphated twice. Most commonly, the hydroxyls of the 4 and 6 positions of the N-acetyl-galactosamine are sulphated, with some chains having the 2 position of glucuronic acid sulphated. Sulphation is mediated by specific sulfotransferases. Sulphation in these different positions confers specific biological activities to chondroitin glycosaminoglycan chains.

Some old classification terminology exists as follows: Chondroitin sulphate A—sulphation site is carbon 4 of the N-acety-lgalactosamine sugar (also known as chondroitin-4-sulphate); Chondroitin sulphate B—an old name for dermatan sulphate, which is no longer classified as a form of chondroitin sulphate; Chondroitin sulphate C—sulphation site is carbon 6 of the N-acetyl-galactosamine sugar (also known as chondroitin-6-sulphate); Chondroitin sulphate D—sulphation sites are carbon 2 of the glucuronic acid and 6 of the N-acety-lgalactosamine sugar (also known as chondroitin-2,6-sulphate); and Chondroitin sulphate E—sulphation sites are carbons 4 and 6 of the N-acety-lgalactosamine sugar (also known as chondroitin-4,6-sulphate). All such derivatives are encompassed herein as "chondroitin sulphate" as contemplated for use in the present invention.

In an embodiment the proteoglycan is present within the second component. In this embodiment it is preferred that the wt/wt ratio of proteoglycan: biocompatible phosphate and/or sulphonamide is 1:3. More preferably, where the proteoglycan is chondroitin sulphate and the biocompatible phosphate and/or sulphonamide is TTP the preferred wt/wt is 1:3.

Therefore, in a further aspect the invention provides a prolonged release delivery system for delivery of a biologically active agent, the system comprising:
(i) a first component comprising chitosan (or suitably functionalised derivatives thereof); and
(ii) a second component comprising tripolyphosphate, wherein
(a) the first and/or second component further comprises the biologically active agent; and
(b) the first and/or second component also comprises:
  (i) hydroxyapatite; and/or
  (ii) chondroitin sulphate; and
whereby the first and second components of the system are physically isolated and, when in use, combining of the first and second components promotes crosslinking and results in the formation of a biopolymer hybrid gel-depot including the biological active agent.

In another aspect the invention further provides a method of forming a prolonged release biopolymer hybrid gel-depot including a biologically active agent, said method comprising:
(i) providing a first component comprising chitosan (or a suitably functionalised derivative thereof) and a second component comprising tripolyphosphate,
  (a) wherein the first and/or second component further comprises the biologically active agent; and
  (b) wherein the first and/or second component also comprises:
    (i) hydroxyapatite; and/or
    (ii) chondroitin sulphate; and
(ii) combining the first and second components for a time and under conditions to promote crosslinking and to form a biopolymer hybrid gel-depot including the biologically active agent.

The Biological Active Agent

The first and/or second component also comprises a biological active agent that can then be administered to a subject to provide a prolonged release of the agent to the subject.

The term "biological active agent" is meant to encompass any molecule either synthetically made or of natural origin known to the skilled person as being able to elicit a desired physiological effect in vivo, for example a pharmaceutical or vaccine having use in the treatment or prevention of a disease or condition, especially one which requires prolonged delivery to a subject.

The biological active agent may be a therapeutic that is required to be administered, for instance, subcutaneously due to problems encountered when such agents are delivered via other routes. Examples of these agents include compounds with poor bioavailability due to poor absorption, high lipophilicity, high molecular weight, and/or excessive net charge as well as agents that are susceptible to enzymatic degradation. These agents encompass physiologically unstable small molecules, peptide or protein therapeutics, antibodies, synthetic hormones, recombinant or killed vaccines, or gene therapeutics.

In one embodiment the biological active agent is selected from but are not limited to peptide hormones such as insulin, cortisol, estrogen or growth hormone; antibodies such as infliximab, adalimumab, nituximab, alemtuzumab, daclizumab or basiliximab; fusion proteins such as etanercept and vaccines against infectious agents, or for immunocastration (LHRH) or other behavioural modifications.

Other specific actives include:
Prednisone an anti-inflammatory steroidal drug very slightly soluble in water
Hydroxycamptothecin, e.g. 10-hydroxycamptothecin, anti-cancer drug to provide tissue (site)-specific delivery and activity with lower interaction with the reticuloendothelial system
Hepatitis B surface antigen HBsAg and Hepatitis B core antigen HBcAg immunisation, particularly to counter the low re-immunization rate (3 injection immunisation schedule) prevalent in developing countries
DNA genetic vaccines plasmid DNA delivery, human immunodeficiciency virus and influenza DNA vaccines, provide DNA protection against nuclease degradation. Drug delivery system for DNAzymes to overcome cell entry and cytotoxicity limitations. Drug delivery systems for siRNA molecules for cancer and other genetic disorders
Delivery of anti-cancer drug doxorubicin to tumor sites The active agent may be present in molecular form (i.e. substantially as molecules dispersed within the gel-depot), or may be in particulate form (i.e. clumps of numerous molecules located proximally within the gel-depot). However, as would be appreciated there are numerous scenarios in which the active agent may be presented within the biopolymer hybrid gel-depot of the present invention. The agent may be encapsulated, present in pores, bound to free amine, carried on a protein, and/or free for an immediate burst effect upon implantation. The exact regime used will depend on the bioactive agent and the application. In addition or alternatively, the bioactive agent may be conjugated to one or more components of the polymer. If conjugated, the active agent may be bound (ionically or covalently) to a carrier molecule present within the gel-depot. For instance, the active agent may be bound to chitosan. It would be appreciated that in this embodiment the active agent may be presented in the first component of the system to prevent premature and unwanted in situ crosslinking with the biocompatible phosphate and/or sulphonamide of the second component prior to injection.

The Biopolymer Hybrid Gel-Depot

With reference to one of the preferred embodiments, the chitosan is able to crosslink with the tripolyphosphate and thereby undergo classical attractive polymer induced solvent depletion resulting in polymer compression and exclusion of liquid phase, i.e. syneresis beyond that resulting from chain-chain crosslinking.

Typically the biopolymer hybrid forms spontaneously from substantially liquid components (including liquid dispersions). That is, prior to the formation of the biopolymer hybrid, the first and second components are not in either the gaseous, semi-solid, or solid forms. Accordingly, preferably the components are presented such that they are easily injectable and this also avoids the need for additional curing mechanisms/apparatuses (eg UV, IR, heat).

The resultant gel-depot is not thermoplastic, nor results from a semi-solid (eg a paste) where no change of form is necessary to form the polymer from its constituents. It may be referred to as a binary solid of inorganic/organic material. The gel-depot of the present invention is characterised as being 'compliant' as expressed by the Young's modulus (a modulus of elasticity). In an embodiment the Young's modulus range for the depot is about 20 to 60 kPa and preferably around 10 kPa. The preferred compressive modulus is in the range of 100 kPa to 500 kPa preferably around 220 kPa.

Preferably the gel-depot is biodegradable, meaning it can be broken down in vivo. Bio-erosion is a similar term. The release profile of an active agent from the gel-depot may include a short- and a long-term portion. The short-term profile may be achieved by free active agent present in the gel-depot, while the long-term profile will rely on the gel-depot biodegradation to gradually release more strongly embedded active agent.

As used herein, the phrase "prolonged release" means that the rate of release of the agent to the subject is slower than would occur if the agent were administered to the subject directly. In one embodiment, the biological active agent is released to the subject for a period of up to about 12 months. The agent may be released continuously or non-continuously over the time period.

The term "controlled release" means that the rate at which the biological active component is released from the polymer into the subject is controlled by such mechanisms as the rate at which the biopolymer-gel depot biodegrades and the mode in which the active agent is contained within the depot (i.e. encapsulated, conjugated, free in solution etc.), other factors include the size and location of the depot.

In an embodiment the % wt/wt ratio range of the specific components within the resulting biopolymer hybrid gel-depot are as follows: biocompatible polyaminosaccharide and/or protein:biocompatible phosphate and/or sulphonamide:aqueous insoluble alkaline earth metal phosphate:biocompatible glycan and/or proteoglycan from about 4:6:1:2 to about 4:12:4:4.

It will be appreciated however that the above ratios may depend, to a limited extent, on the processing conditions (including batch sizes) since it is a kinetic mass controlled transport process. Outside this range a depot with very different properties may be made which might have special advantageous applications other than those envisaged herein (e.g. softer or harder gels).

Accordingly, in a further aspect the invention provides a biopolymer hybrid gel-depot comprising
 (i) a biocompatible polyaminosaccharide and/or protein;
 (ii) a biocompatible phosphate and/or sulphonamide substantially crosslinked to (i);
 (iii) an aqueous insoluble alkaline earth metal phosphate;
 (iv) a biocompatible glycan and/or proteoglycan; and
 (v) a biologically active agent.

In a further aspect, the invention provides a biopolymer hybrid gel-depot comprising:
 (i) chitosan (or suitably functionalised derivatives thereof);
 (ii) tripolyphosphate substantially crosslinked to (i);
 (iii) hydroxyapatite;
 (iv) chondroitin sulphate; and
 (v) a biologically active agent.

Further Components

The biopolymer hybrid gel-depot of the present invention may also comprise an adjuvant. An adjuvant modulates an immune response to attain a more durable and higher level of immunity using smaller amounts of antigen or fewer doses than if the antigen were administered alone.

Various adjuvants are known to those skilled in the art. Examples of adjuvants include incomplete Freunds adjuvant (IFA), Adjuvant 65 (containing peanut oil, mannide monooleate and aluminium monostrearate), oil emulsions, Ribi adjuvant, the pluronic polyols, polyamines, Avridine, Quil A, saponin, MPL, QS-21, and mineral gels such as aluminium salts. Other examples include oil in water emulsions such as SAF-1, SAF-0, MF59, Seppic ISA720, and other particulate adjuvants such as ISCOMs and ISCOM matrix.

In addition, the active agent and/or gel-depot may include further amounts of pharmaceutically acceptable and suitable carriers, diluents, or excipients. These include all known solvents, dispersion media, fillers, solid carriers, castings, antifungal and antibacterial agents, surfactants, isotonic and absorption agents and the like. It will be understood that the active agent and/or gel-depot may also include other supplementary physiological active agents.

Administration to a Subject

The system as described above preferably includes the use of solutions and suspensions of the two components such that they are easily injectable to the subject. The system is designed such that the first and second components are separated (physically isolated) until just prior to use. In a preferred embodiment, the first and second components are combined just prior to injection, for instance, with the use of a dual compartmentalised syringe with a single injection needle. Separating the two components in such a system would prevent/minimise needle blockage as the components rapidly cross-link. Accordingly, it would be appreciated that while preferably the majority of the gel-depot formation takes place in vivo, at least some of the gel-depot may form in the syringe chamber or needle during injection as the first and second components combine.

Also coinjection may be used using a specially designed dual needle with separate passages for two constituents that allow the mixing to occur upon meeting at the mouth of the needles.

In another embodiment the invention also contemplates the possibility that the first and second components are injected simultaneously or sequentially at the same site in vivo. It would be appreciated however that this type of administration may not be preferable if one of the components is rapidly absorbed into the biological system.

Accordingly in a further aspect the invention provides a method of delivering a biologically active agent to a subject including the step of administering:
 (i) a first component comprising a biocompatible polyaminosaccharide and/or protein; and
 (ii) a second component comprising a biocompatible phosphate and/or sulphonamide compound capable of crosslinking with the first component,
wherein
(a) the first and/or second component further comprises the biologically active agent; and
(b) the first and/or second compounds also comprises:
 (i) an aqueous insoluble alkaline earth metal phosphate; and/or
 (ii) a biocompatible glycan and/or proteoglycan; and
whereby the first and second components are simultaneously or sequentially injected at the same site.

As a further possibility, it is contemplated that the system could be used to form gel-depot based implants which are manufactured for injection in vivo. That is, the gel-depot may be formed ex vivo and then implanted.

Accordingly, in a still a further aspect the invention provides a method of delivering a biologically active agent to a subject including the step of implanting a biopolymer hybrid gel-depot comprising:
 (i) a biocompatible polyaminosaccharide and/or protein;
 (ii) a biocompatible phosphate and/or sulphonamide substantially crosslinked to (i);
 (iii) an aqueous insoluble alkaline earth metal phosphate;
 (iv) a biocompatible glycan and/or proteoglycan; and
 (v) a biologically active agent.

In relation to the preferred delivery mode as described above, it is preferred that crosslinking and gel-formation occurs rapidly and within 1-5 seconds after combining of the first and second components. More preferably, the gel-depot is formed 1-2 seconds after combining of the first and second components.

The in vivo injection according to the present invention may be subcutaneous, intramuscular or intraperitoneal. Preferably the invention is directed to a subcutaneous delivery system.

As mentioned above, the biopolymer hybrid gel-depot has application in the administration of a biologically active agent, such as a pharmaceutical drug or vaccine.

The biopolymer hybrid gel-depot may formed in vivo or implanted into the subject in order to treat or prevent a disease or condition. As used herein the terms "treating" and "preventing" mean any treatment of prevention of a disease or condition in a subject. "Treatment" and "prevention" includes: (a) inhibiting the disease or condition, i.e., arresting its development; or (b) relieving or ameliorating the symptoms of the disease or condition, i.e., cause regression of the symptoms of the disease or condition. The effect may be therapeutic in terms of a partial or complete cure of the disease or condition.

"Disease" as used herein is a general term used to refer to any departure from health in which a subject suffers and which can be treated or prevented using a gel-depot which provides prolonged release of an active agent. A "condition" refers to an abnormal function of part of the body of a subject and which can be treated or prevented using a gel-depot which provides prolonged release of an active agent.

The subject in which a disease or condition is to be treated or prevented may be a human or a mammal of economical importance and/or social importance to humans, for instance, carnivores other than humans (such as cats and dogs), swine (pigs, hogs, and wild boars), ruminants (such as cattle, oxen, sheep, giraffes, deer, goats, bison, and camels), horses, and birds including those kinds of birds that are endangered, kept in zoos, and fowl, and more particularly domesticated fowl, eg., poultry, such as turkeys, chickens, ducks, geese, guinea fowl, and the like, as they are also of economical importance to humans. The term does not denote a particular age. Thus, both adult and newborn subjects are intended to be covered.

As used in the subject specification, the singular forms "a", "an" and "the" include plural aspects unless the context clearly dictates otherwise. Thus, for example, reference to a "virus" includes a single viral particle as well as two or more viral particles, "a gene" includes a single gene or two or more genes. Reference to "the invention" includes single or multiple aspects of the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

Further features of the present invention are more fully described in the following non-limiting examples.

EXAMPLES

Materials Used

Low molecular weight chitosan (~150 kDa) with a viscosity at 1 wt. % chitosan in 1% acetic acid at 20° C. of ~100 mPa·s was sourced from Sigma-Aldrich and used in all polymer formulations of these Examples. The sodium tripolyphosphate (technical grade, 85%), hydroxyapatite (type I suspension in 0.001 M phosphate buffer pH 6.8 at 26 wt % total solids) and chondroitin sulphate A (sodium salt from bovine trachea, ~70% cell culture tested, with the balance chondroitin sulphate C) were sourced from Sigma-Aldrich Chemicals.

REFERENCE EXAMPLES

Reference Example 1

Chitosan/Hydroxyapatite 1 wt % and 2 wt % chitosan solutions in 1 vol % acetic acid were obtained. Either 100, 200 or 300 µL of the 26 wt % hydroxyapatite in phosphate buffer was added to 5 mL of the chitosan solutions. The 1 wt % chitosan solution combined with the hydroxyapatite did not produce a gel. The 2 wt % chitosan solution on the other hand, when combined with the 26 wt % hydroxyapatite to produce 25 wt %, 50 wt % and 75 wt % hydroxyapatite:chitosan mixtures, respectively, did form gels. To clarify, a 25 wt % hydroxyapatite to chitosan solution contains 25 g of hydroxyapatite per 100 g of chitosan.

In all cases the mixtures were subjected to an initial vigorous stirring and then left at room temperature for 12 hours.

The 50 wt % and 75 wt % hydroxyapatite:chitosan mixtures resulted in uniform hard gels while the 25 wt % hydroxyapatite:chitosan mixture remained as a viscous liquid after the 12 hours. We believe this demonstrates the ability of the phosphate groups on the surface of the hydroxyapatite particles to participate in cross-linking with the basic nitrogen-containing groups on the chitosan chains in solution. That is, in the weakly acidic conditions of the chitosan solution the protonated amine groups of the chitosan likely provide cross-linking with the phosphate groups on the hydroxyapatite particle surface. Hydroxyapatite may also dissolve slightly in these mild acidic conditions. The products are best described as uniform granular solids and are shown in FIG. 1.

Figure 2:
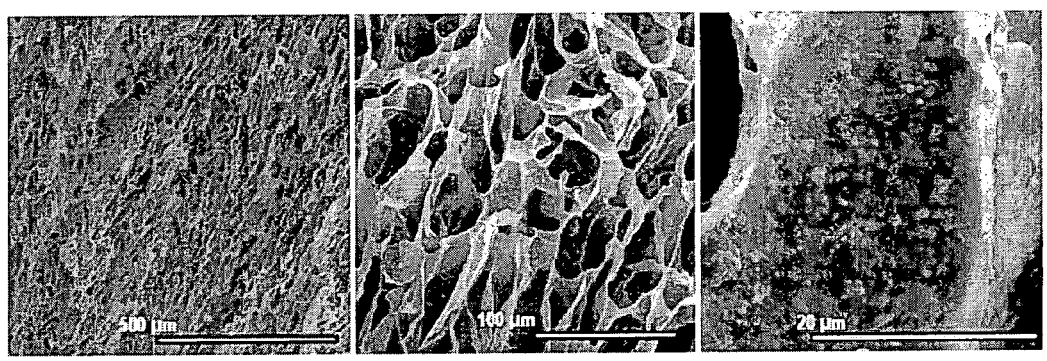
FIG. 2 Images of a freeze dried chitosan/hydroxyapatite gel (reference example 1).

The freeze dried microstructure of the gel products was studied using Scanning Electron Microscopy (SEM) as seen in FIG. 2. The uniform gel produced contained all the water present in the initial solution in large cavities produced during the gelation process. The chitosan-hydroxyapatite gel microstructure shows this cross-linking of the Hydroxyapatite particles with the chitosan chains in solution.

Reference Example 2

Chitosan/Hydroxyapatite/Tripolyphosphate Depot

Volumes of hydroxyapatite suspension ranging from 50 to 400 µL were added to 5 mL of 2 wt % chitosan in 1% acetic acid solution with vigorous stirring. A tripolyphosphate solution was prepared in various concentrations ranges between 2 and 80 mM. Then, under a slow stirring rate, 5 mL of each tripolyphosphate solution was added to each chitosan-hydroxyapatite mixture. Tripolyphosphate in general is a more active and much faster cross-linking entity than particulate hydroxyapatite in solution. Thus, tripolyphosphate was introduced as a potential cross-linker to provide a firm but less rigid polymer.

Figure 3:
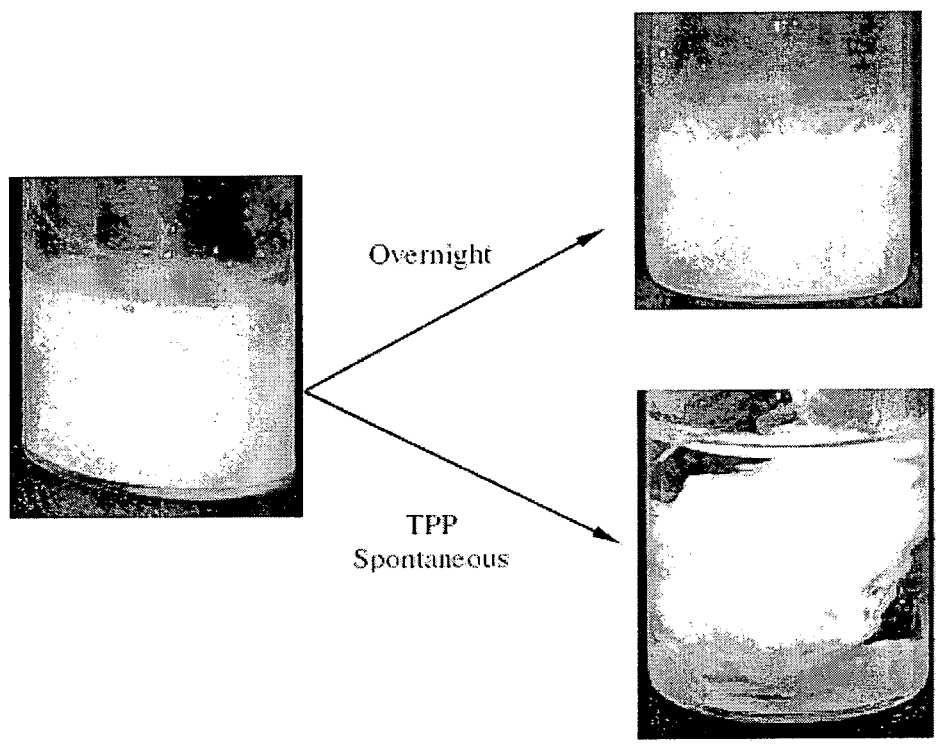
FIG. 3 A photographic image of the gelation of chitosan/hydroxyapatite suspension with and without tripolyphosphate as the cross-linking solution (reference example 2).
Figure 4:
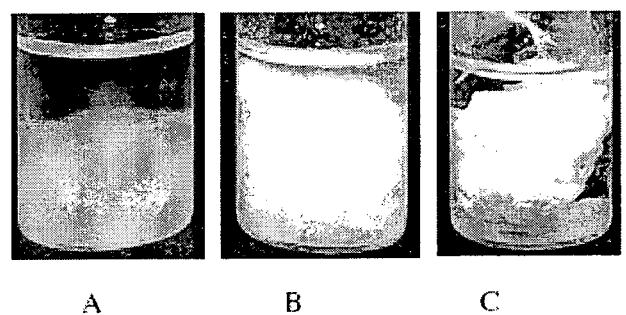
FIG. 4 A photographic image of chitosan/hydroxyapatite/tripolyphosphate gels (reference example 2) produced by cross-linking with tripolyphosphate; (A) precipitate formed at low tripolyphosphate concentration, (B) mixture of precipitate and uniform gel formed at medium concentrations of tripolyphosphate, (C) uniform complaint gel formed at high concentrations of tripolyphosphate.

In general, and in comparison to Reference Example 1, the gelation process using tripolyphosphate occurred almost instantaneously. As well, the gelation of chitosan-hydroxyapatite suspension using tripolyphosphate solution produced a uniform gel than in the absence of tripolyphosphate as the images in FIG. 3 demonstrate. Gels with very different characteristics were obtained across the hydroxyapatite:chitosan and tripolyphosphate ranges, all of which demonstrated high syneresis (volume contraction) effects upon spontaneous gel formation. At low concentrations of tripolyphosphate, the mixture formed a precipitate together with a clear supernatant as shown in FIG. 4A. At high concentrations of tripolyphosphate uniform compliant gels and clear supernatant solutions were observed as seen in FIG. 4C. A combination of these was observed between these two limits as in FIG. 4B.

Figure 5:
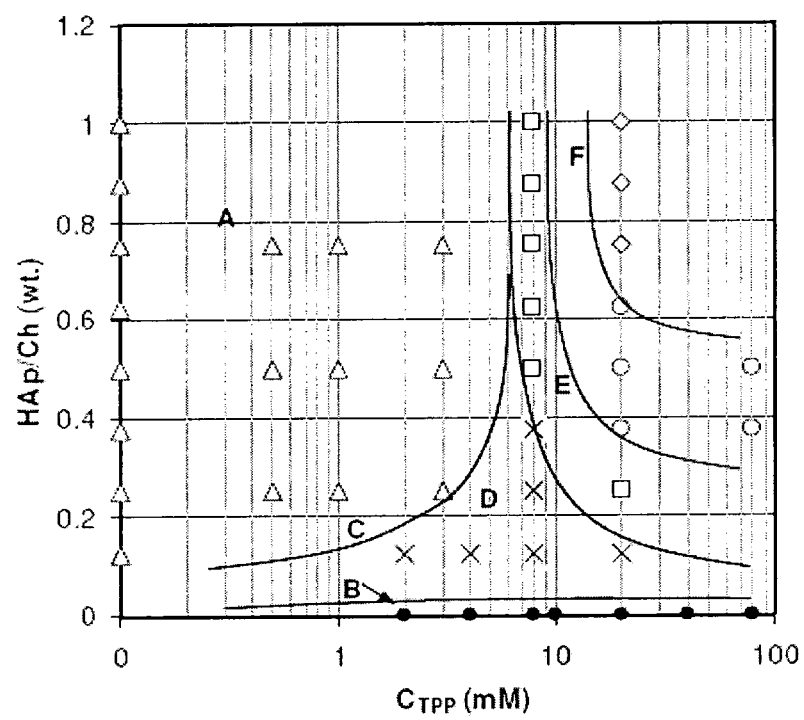
FIG. 5 A schematic illustration of chitosan/hydroxyapatite gels (reference example 2) produced by cross-linking with tripolyphosphate. 5 mL of chitosan solution was mixed with hydroxyapatite suspension (26% wt) then 5 mL of tripolyphosphate cross-linker solution was added with gentle stirring, where (A) is viscose emulsion, (B) membrane gel, (C) cloudy precipitate, (D) gel, (E) strong gel, and (F) fibrous gel.

A semi-quantitative assessment of the physical properties of the depot gels was made by observing their appearance and elasticity and plotting these on a pseudo phase diagram (FIG. 5). The gels produced were classified as either (A) a viscose emulsion, (B) a membrane gel, (C) a cloudy precipitate, (D) a gel, (E) a strong gel, and (F) a fibrous gel.

In the optimum compositional range with slow mixing, gelation was found to occur spontaneously yielding a strong white gel containing all the hydroxyapatite particles and with syneresis driving the clear liquid phase (chitosan depleted) out as a surrounding fluid. On one side of this compositional domain (lower tripolyphosphate) weaker gels were formed and on the other side (higher tripolyphosphate) fibrous gels were formed. The syneresis phenomenon produced a more dense material with lower porosity compared to the gel formed without tripolyphosphate cross-linking. A gel with the necessary properties only occurs at higher hydroxyapatite:chitosan ratios and higher concentrations of tripolyphosphate.

Figure 6:
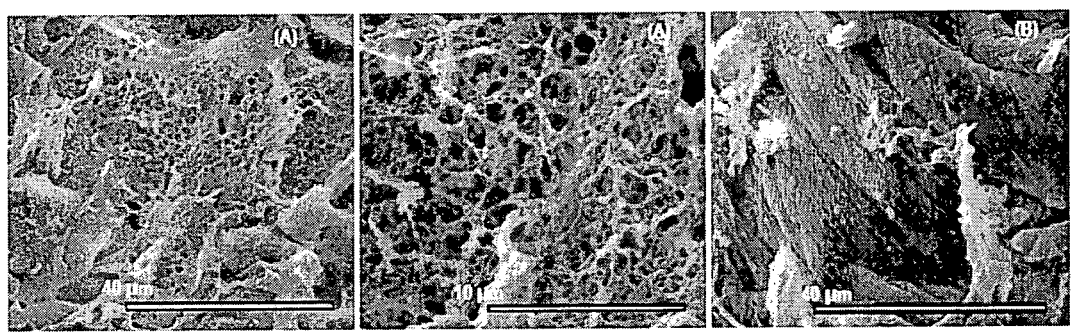
FIG. 6 Images of freeze dried chitosan-Hydroxyapatite-tripolyphosphate gel (reference example 2); (A) show a fractured cross section and (B) shows the outer layer of the gel.
Figure 7:
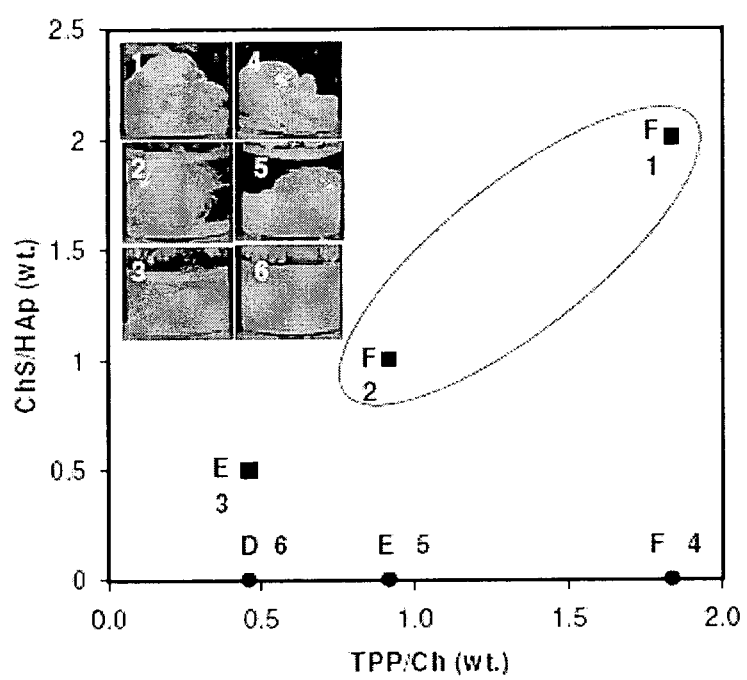
FIG. 7 The chitosan/hydroxyapatite/tripolyphosphate/chondroitin sulphate (example 1) and chitosan/hydroxyapatite/tripolyphosphate gels (reference example 2) represented as a pseudo phase diagram. The area between F1 and F2 represents the most appropriate composition for depot formation. The labels (D) gel, (E) strong gel, and (F) fibrous gel conform to FIG. 5.

SEM images of an example gel are shown in FIG. 6. The formation of two different structures during the gel formation process is seen; the first is the porous bulk of the gel (FIG. 6A) and the second is a low porosity outer layer (FIG. 6B).

When tripolyphosphate solution was added to chitosan solution only (i.e. no hydroxyapatite) a membrane of the cross-linked chitosan forms between the two solutions upon mixing, preventing the formation of a uniform gel.

EXAMPLES OF THE INVENTION

Example 1

Chitosan/Hydroxyapatite/Chondroitin Sulphate/Tripolyphosphate Depots

A mixture of 40 pt of the hydroxyapatite suspension and 2 mL of a 2 wt % chitosan in 1% acetic acid solution was prepared. A 1% chondroitin sulphate in 100 mM tripolyphosphate solution was also prepared. 0.5, 1, or 2 mL of the chondroitin sulphate solution was added to the hydroxyapatite:chitosan mixture with slow stirring at room temperature.

Chondroitin sulphate is a polymer salt soluble in water, and it precipitates under acidic conditions, therefore it was initially dissolved in the tripolyphosphate cross-linker solution prior to addition to the hydroxyapatite:chitosan mixture and spontaneous gelation.

Figure 8:
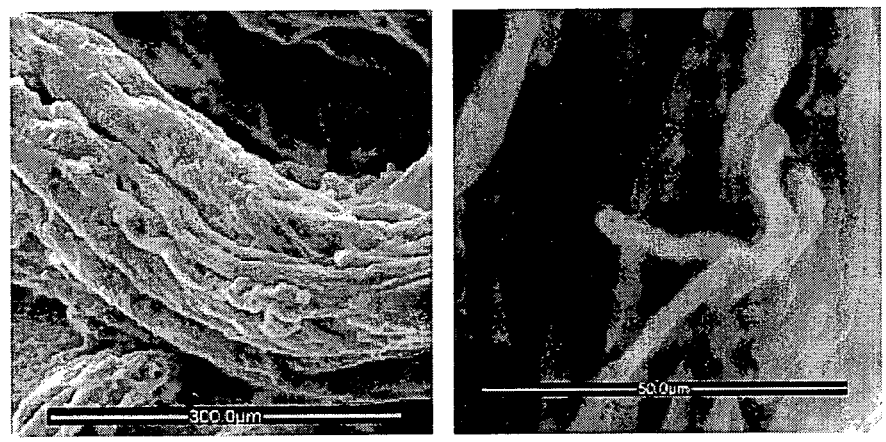
FIG. 8 Images of chitosan/hydroxyapatite/chondroitin sulphate (example 1) cross-linked using tripolyphosphate at 60% humidity (5 Torr water vapour pressure).
Figure 9:
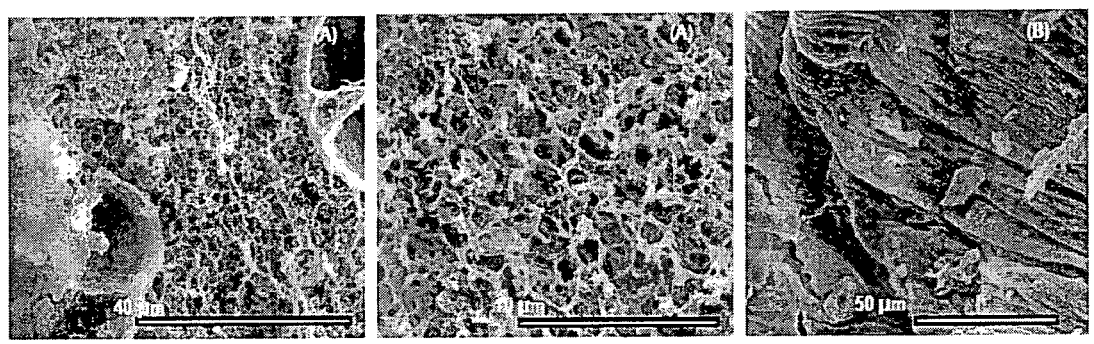
FIG. 9 SEM images of freeze dried chitosan/hydroxyapatite/tripolyphosphate/chondroitin sulphate gel (example 1); (A) shows a fractured cross-section and (B) shows outer surface of the gel.

The gels formed in this process are similar in physical properties to the chitosan-Hydroxyapatite-tripolyphosphate gels. The images in FIG. 8 show that chitosan/hydroxyapatite/chondroitin sulphate/tripolyphosphate gels have light brown colour compared to the similar gels without chondroitin sulphate in their composition, and the plot indicates the preferred compositional ranges for depot formation. In the optimal compositional range, a light brown compliant hydrogel formed spontaneously together with a clear depleted liquid phase. The chitosan-chondroitin sulphate-hydroxyapatite-tripolyphosphate gel microstructure showed similar structure to those with chitosan-Hydroxyapatite-tripolyphosphate (see FIG. 9).

FIG. 9A shows the porous bulk of the gel and FIG. 9B shows the lower porosity outer surface. The fibre-like formations are likely due to stirring during the gelation process.

Example 2

Injectable Depot Gels Incorporating Chitosan Particles

Figure 10:
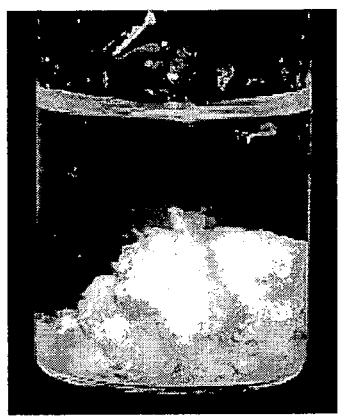
FIG. 10 Photographic and SEM images of a polymer gel incorporating nano- and microparticles (example 2): (A) compliant gel and clear excluded liquid phase, and (B) the incorporation of particles within the cell wall structure.
Figure 10:
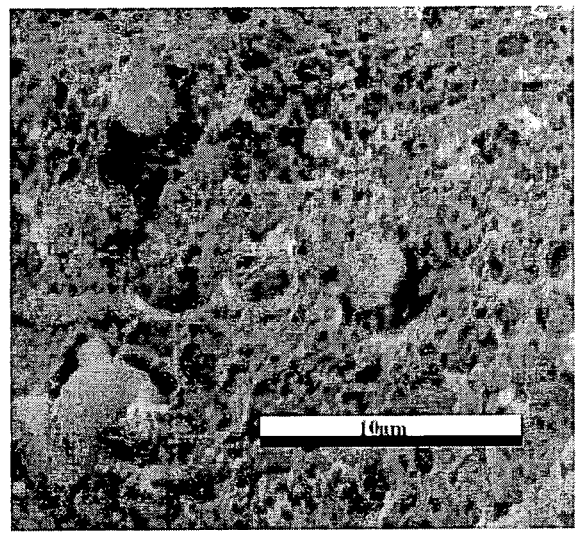

The final composition of the polymer including chitosan was: soluble chitosan and chondroitin sulphate, hydroxyapatite (as nanoparticles), and tripolyphosphate (as the primary cross-linking entity), together with chitosan particles in the range 500 nm to 3 micron (capable of incorporating the vaccine, adjuvant or drug but not doing so in the example). Solutions, suspensions and particles were prepared as above and spontaneous gelation allowed to occur. FIG. 10 A shows the gel formed upon mixing, with the clear liquid phase excluded by syneresis. All biopolymer particles are clearly taken up within the gel microstructure as seen in FIG. 10 B.

The injectability and spontaneous gelation upon co-injection of the polymer components was demonstrated with chitosan:hydroxyapatite suspensions and tripolyphosphate cross-linker solutions using needles and plastic syringes. Silicone oil was used to provide an inert transparent medium in which the processes of gel formation and syneresis could be examined.

Figure 11:
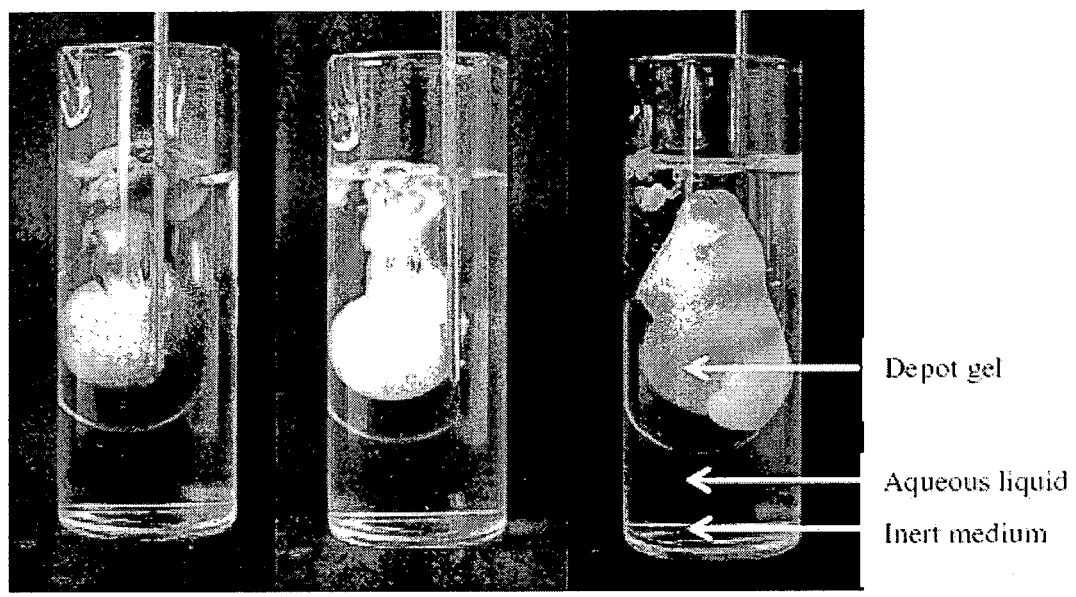
FIG. 11 A photographic image illustrating the In vitro co-injection of depot gel components (over time) and spontaneous formation of gel at needle tips.

FIG. 11 shows these stages and the phases formed. Within the silicone oil medium, the white gel phase can be seen surrounded by a clear aqueous phase representing the liquid excluded from the gel as it undergoes volumetric reduction.

Example 3

Chitosan-HAp

ChS-TPP Depot

Figure 12:
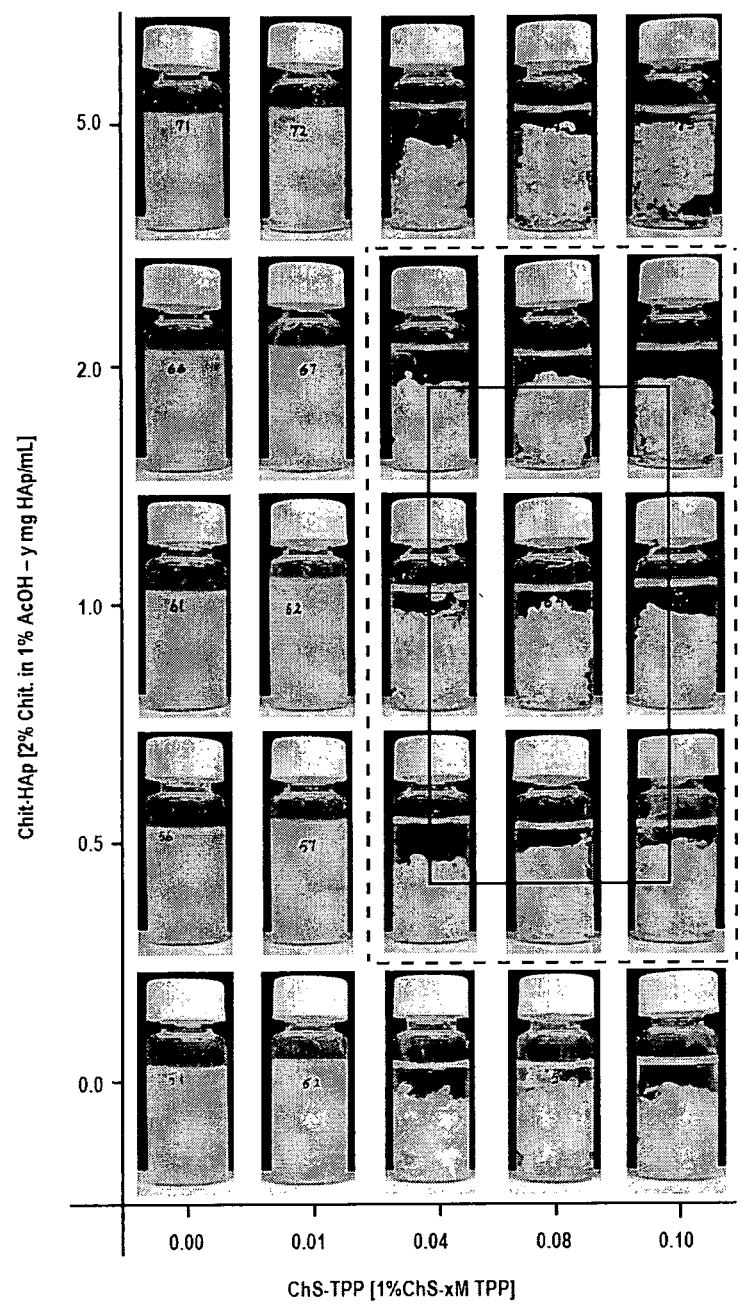
FIG. 12 A photographic representation of Chitosan (Chit)—Hydroxyapatite (HAp) concentration as a function of Chondroitin sulphate (ChS)—Tripolyphosphate (TPP) concentration. Gel compositions within the dashed lines represent the preferred compositions and those within the solid lines represent even more preferred compositions.

The following Depot compositions were investigated:
Component A: 2 wt % chitosan in 1 vol % AcOH in which the HAp wt % was varied
Component B: 1% wt ChS in water in which the TPP (M) was varied
The optimum concentrations are diagrammatically set out in FIG. 12.

Figure 13:
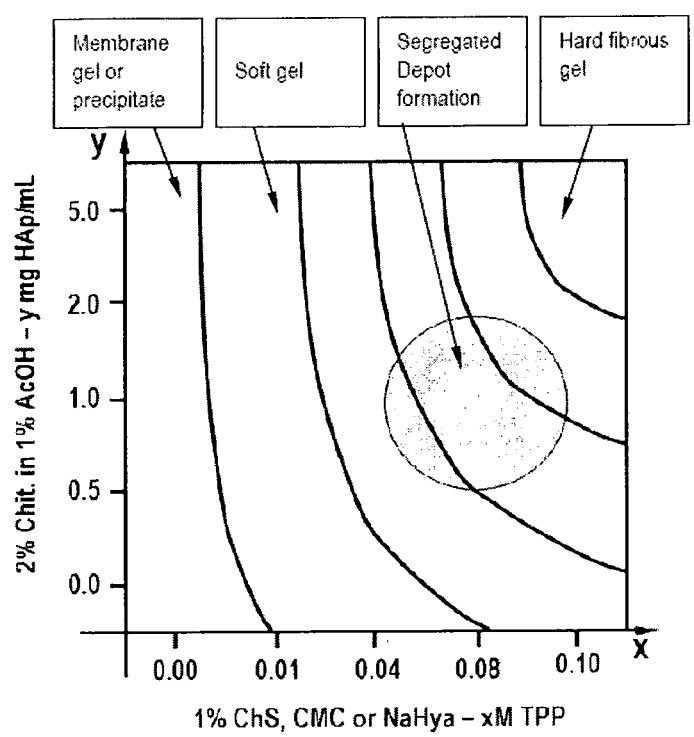
FIG. 13 Phase diagram which represents Chitosan (Chit)—Hydroxyapatite (HAp) concentration as a function of Chondroitin sulphate (ChS)—Tripolyphosphate (TPP) concentration.

The preferred composition is similar to the Depot composition formed without the ChS ie Chit-HAp-TPP as given previously in Example 2. The phases can be represented diagramatically based on the hydrogel formation resulting from A and B components in the above series (see FIG. 13).

Example 4

Mechanical Properties of the Depot Gels

The compressive modulus and the Young's modulus were measured for a suite of depot compositions in systems that did not contain Chondroitin sulphate i.e Chit-HAp-TPP and depot systems that contained Chondroitin sulphate i.e. Chit-HAp-ChS-TPP. Depots were formed as thin layed structures at the various compositions then, while hydrated circular discs of thickness ~1 mm were cut and characterised on a Perkin Elmer differential thermal analysis DMTA instrument.

Figure 14:
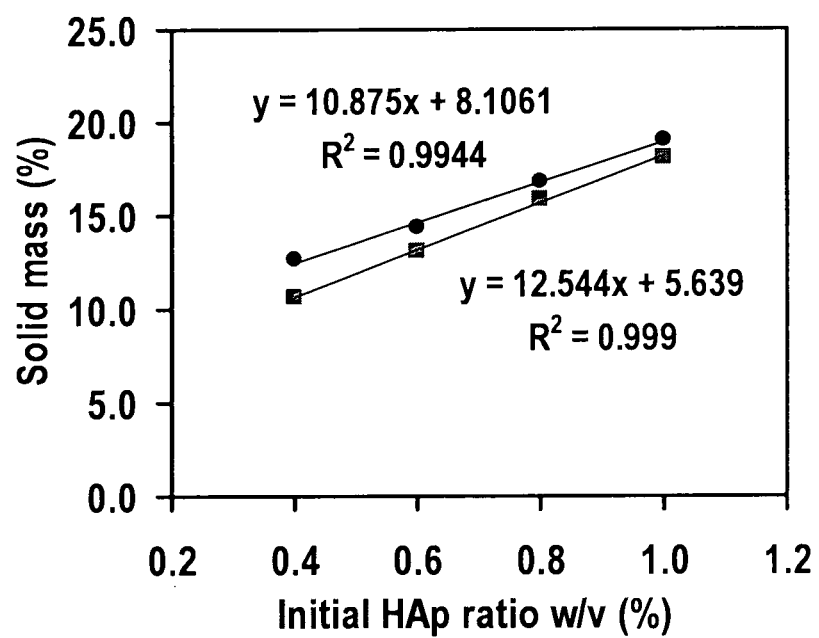
FIG. 14 Graph depicting solid mass (%) as a function of initial HAp ratio of w/v (%).

Since accurate mechanical modulus measurements require the samples to be formed as whole bodies of the soft hydrogel, the planar configuration was adopted rather than formation at the tip on injection needles. This necessitated formation at HAp ratios beyond the initial HAp ratio for preferred depot formation and extrapolation to the preferred composition range. The water contents of these depot hydrogel samples The water content of these hydrogels varied linearly with hydroxyapatite content as shown in FIG. 14.

Figure 15A:
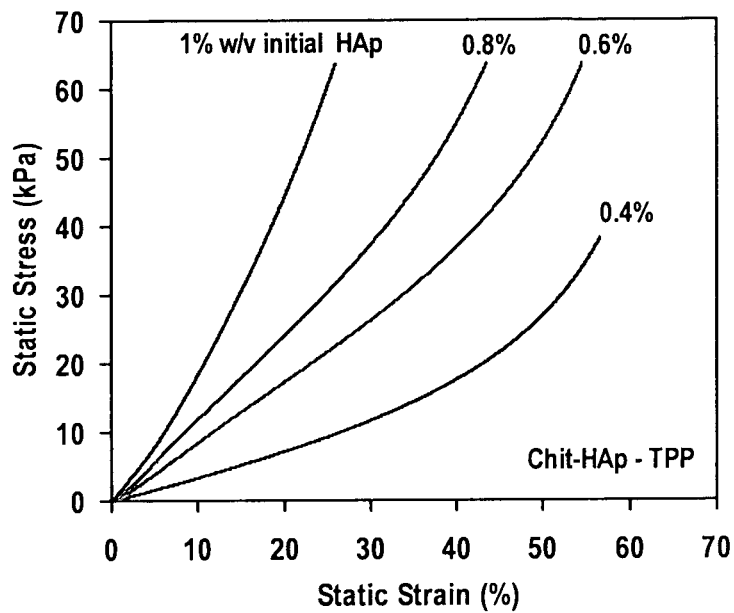
FIGS. 15a and 15b Graphs depicting static stress (kPa) as a function of static strain (%) for various HAp contents.
Figure 15B:
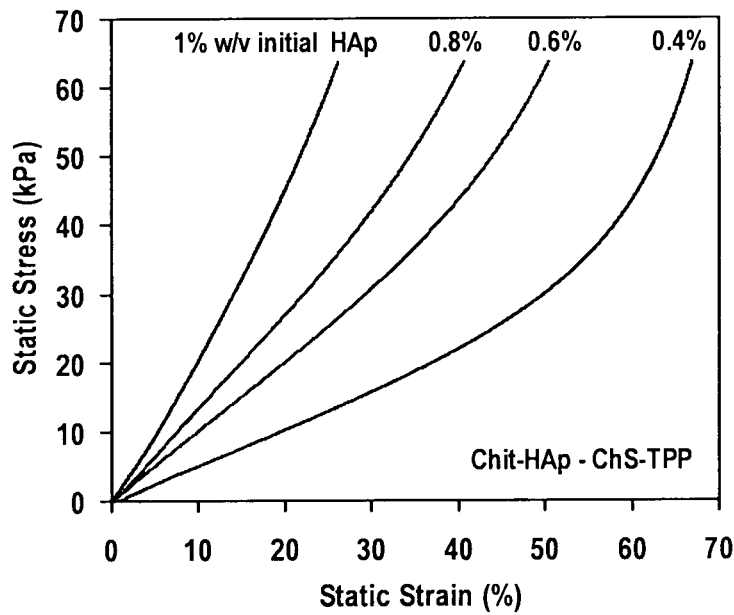

FIGS. 15a and 15b depict the stress—strain curves which were obtained for various Hap contents of the depot gels.

Figure 16A:
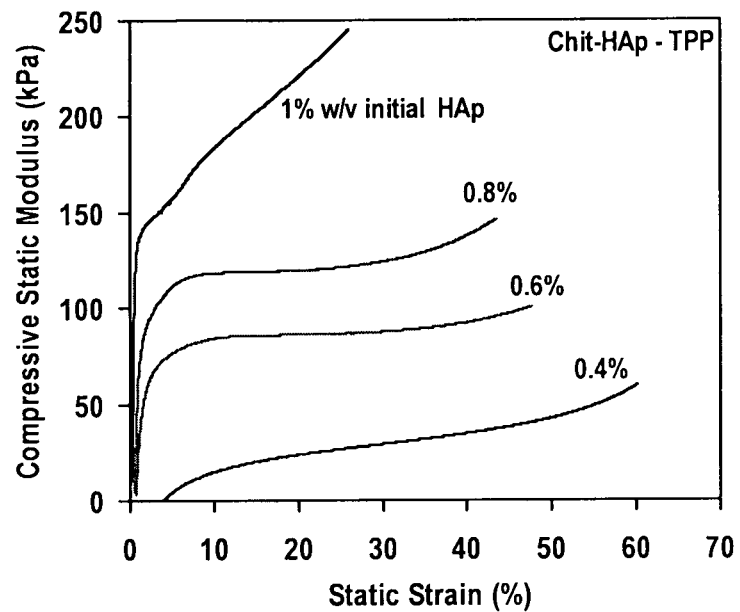
FIGS. 16a and 16b Graph depicting compressive static modulus (kPa) as a function of static strain (%) for various HAp contents.
Figure 16B:
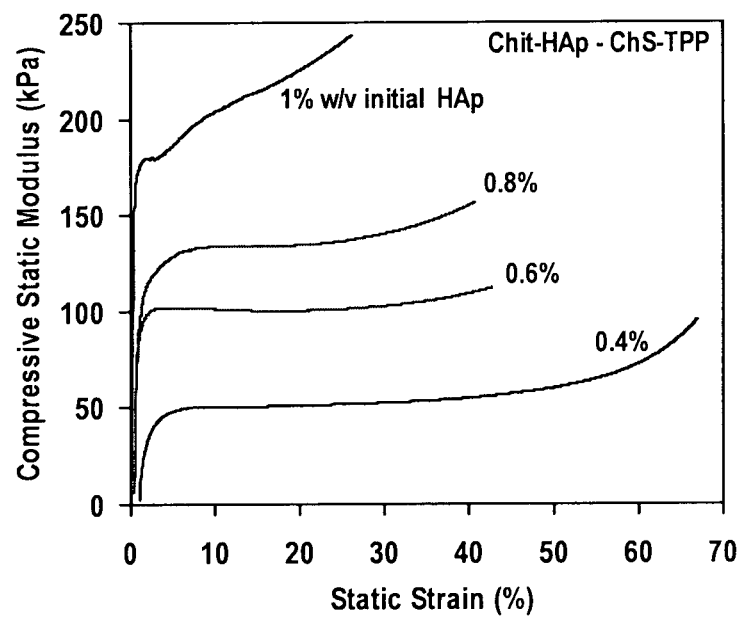

These gave the corresponding compressive static modulus of the two systems as shown in FIGS. 16a and 16b.

Figure 17A:
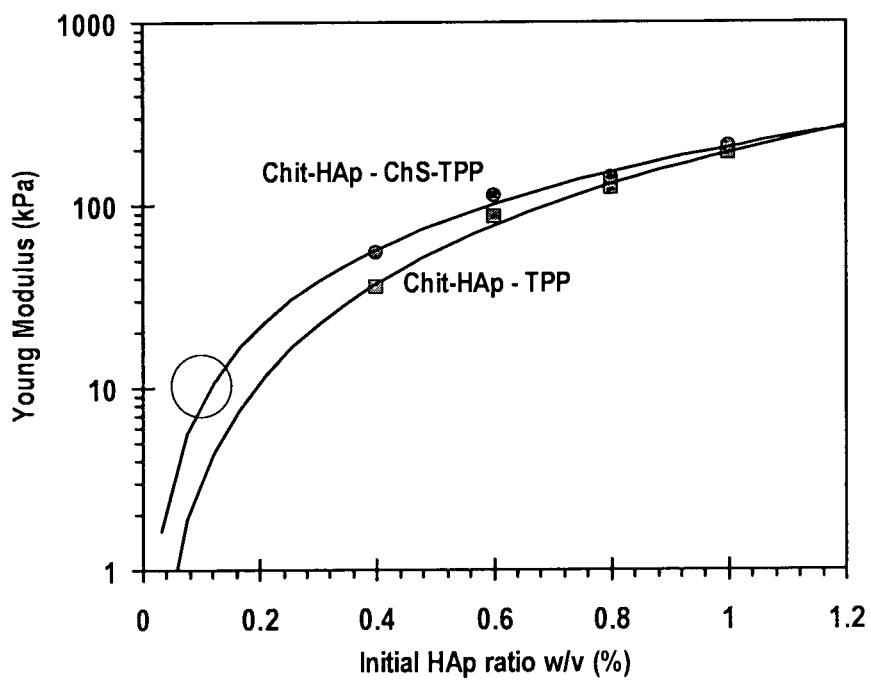
FIG. 17a Graph depicting Young Modulus (kPa) as a function of Initial HAp ratio w/v (%).
Figure 17B:
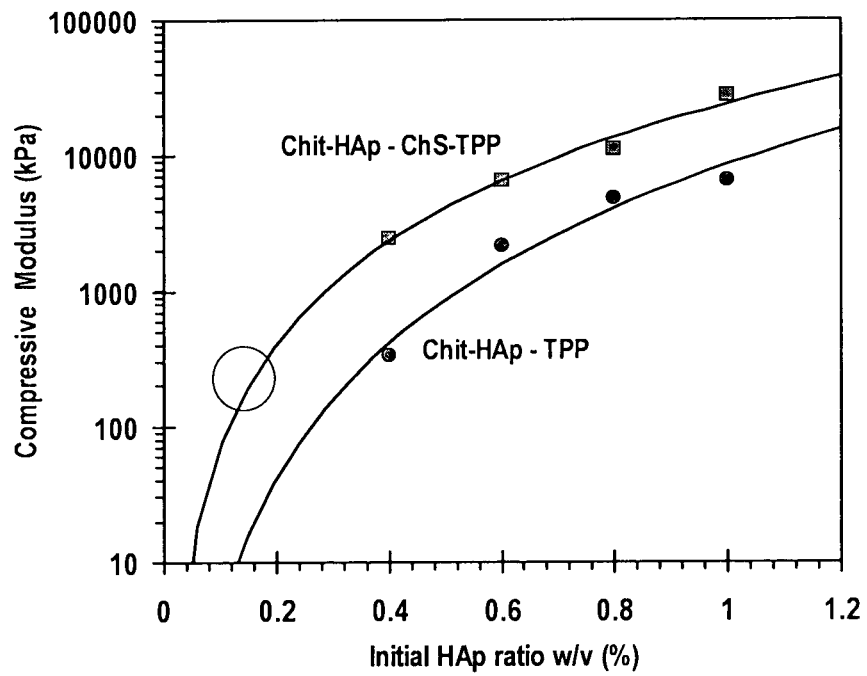
FIG. 17b Graph depicting Compressive Modulus (kPa) as a function of Initial HAp ratio w/v (%).

Finally, the Young's modulus and the compressive modulus where plotted as the initial HAp ratio was varied, and the extrapolated moduli values in the preferred composition range of the injectable gels indicated, as seen below. This gave a preferred Young's modulus in the range 6 kPa to 20 kPa with a mean of 10 kPa, and a preferred compressive modulus in the range 100 kPa to 500 kPa with a mean of 220 kPa. This is indicated in the shaded areas in FIGS. 17a and 17b.

Example 5

CMC as an Alternative to ChS

Figure 18A:
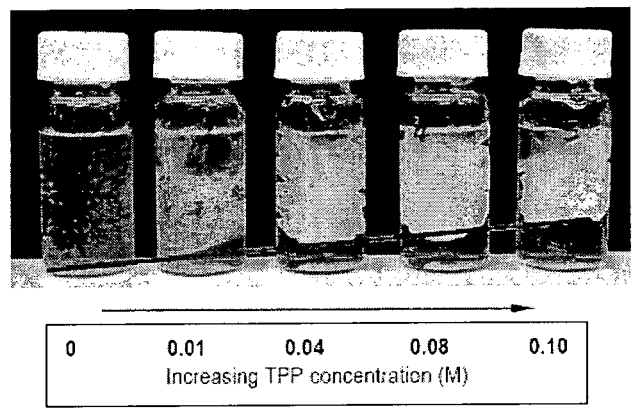
FIG. 18a A photographic representation of gel formation at increasing TPP concentration (M).

The following composition variations were investigated:
Component A: 2% chitosan in 1% AcOH in which the HAp % was varied
Component B: 1% CMC in water in which the TPP (M) was varied The chitosan—HAp suspension was formed using a homogenizer (18 mm stator at 14,100 s$^{-1}$ shear rate) for 2 min. To this an equal volume of component using an Eppendorf pipette dispenser. Photos of the mixture were taken before and after shaking the vial (2-3 min) and after 20 hours (aged depot formation). As the concentration of TPP was increased, the membrane gel changed progressively to a more dense lower volume gel Depot which had a structure related to the diameter of the dispenser (see FIG. 18a).

Figure 18B:
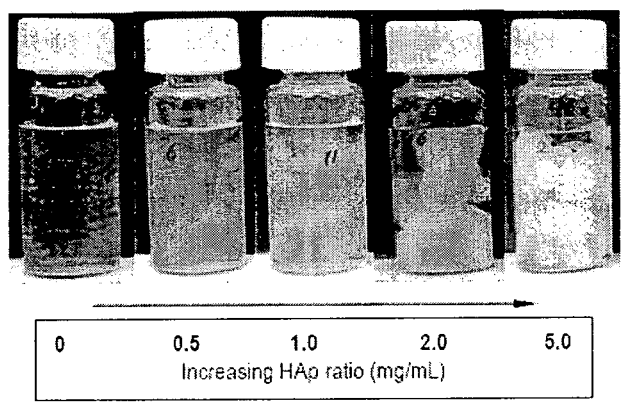
FIG. 18b A photographic representation of gel formation at increasing HAp ratio (mg/mL).

When no TPP crosslinker was added to the systems containing 1% CMC (see below), diffuse membrane gels were formed when chitosan solution [vial 1 FIG. 18b] or chitosan together with HAp suspension [vials 6, 11, 16, 21] were added. This illustrates the electrostatic association of the positively charged chitosan and negatively charged CMC polymer chains. More open gel structures are made in the absence of TPP crosslinker (as illustrated in the previous series with increasing TPP-above).

Figure 18C:
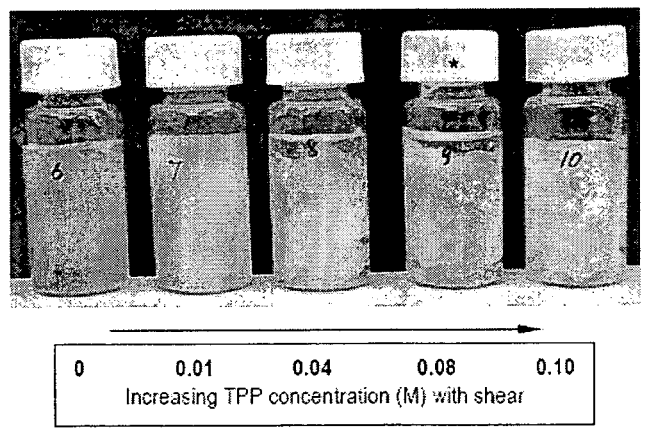
FIG. 18c A photographic representation of gel formation at increasing TPP (M) with shear.

After shear of the mixtures, clearer supernatants were observed at 0.08 M TPP as seen in vial [9] in series 6 to 10 shown in FIG. 18c.

Figure 19:
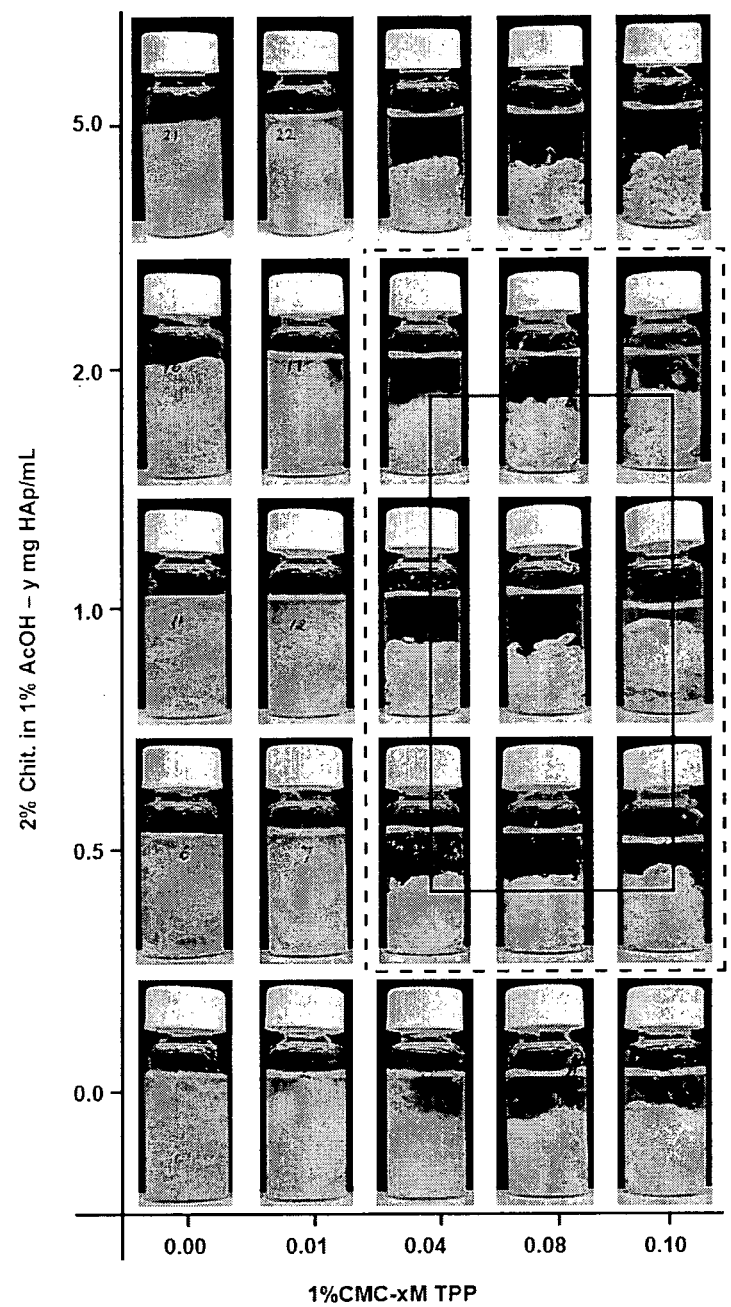
FIG. 19 A photographic representation of Chitosan (Chit)—Hydroxyapatite (HAp) concentration as a function of carboxymethyl cellulose (CMC)—TPP concentration. Gel compositions within the dashed lines represent the preferred compositions and those within the solid lines represent even more preferred compositions.

This optimum TPP concentration, 0.08 M, can be seen at all series as seen in [vials 4, 9, 14, 19, 24] shown in FIG. 19 which suggests that the crosslinking stoichiometry is close to equivalent point (titration end point). The following composition range with CMC as a component indicates the region of preferred depot formation.

After 20 h resting, the gels appear to shrink further as seen in FIG. 19.

The preferred composition is similar to the depot composition without the CMC ie Chit-HAp-TPP as given previously.

Example 6

Na Hyalauronate as an Alternative to ChS

The following composition variations were investigated:
Component A: 2% chitosan in 1% AcOH in which the HAp % was varied
Component B: 1% NaHya in water in which the TPP (M) was varied The array of depot syntheses shows that the depot can be formed using NaHya as an alternative to ChS. This trend suggests that any negatively charged polymer may substitute for the ChS, and thus provide the electrostatic bonding component that induces a pliable depot.

Figure 20A:
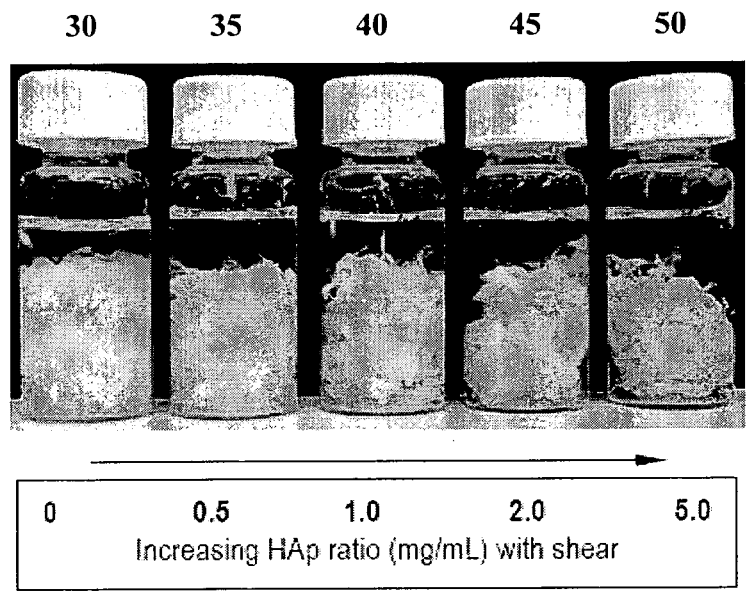
FIG. 20a A photographic representation of gel formation at increasing HAp ratio (mg/mL) with shear.

The hydrogel depot formulations became darker when higher ratios of HAp were used. For example, in 0.1 M TPP with increasing HAp ratio [vials 30, 35, 40, 45 and 50] this trend can be seen (FIG. 20a). Also the volume of the gel decreased (indicating an increased gel Depot density) as the HAp ratio was increased due in part to the increasing contribution of the HAp to the degree of crosslinking.

Figure 20B:
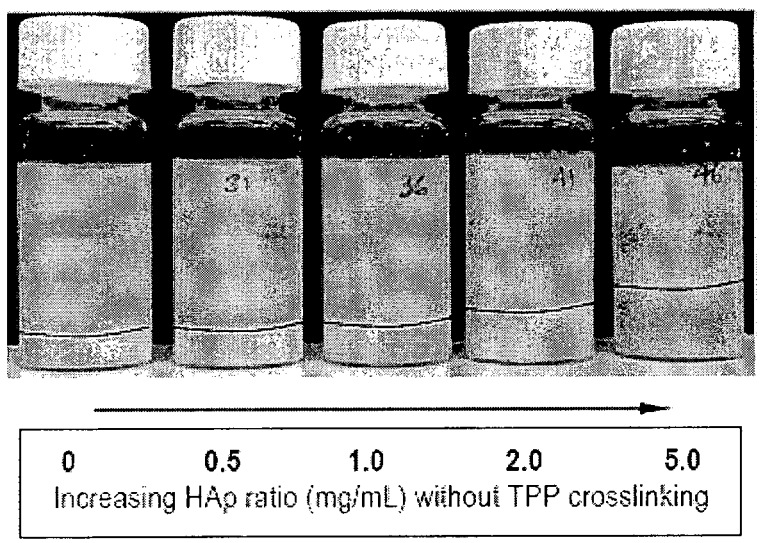
FIG. 20b A photographic representation of gel formation at increasing HAp ratio (mg/mL) without TPP crosslinking.

When no TPP crosslinker was added to the systems, the product was a cloudy suspension in which the larger particles formed a sediment (as seen in FIG. 20b) indicating only the level of association between chitosan and NaHya. The increasing sediment level with increasing TPP clearly shows the TPP particles acting as crosslinking sites transferring Chit chains from solution to sediment.

A cloudy precipitate formed when no TPP crosslinker was used in the composition, which is due, again, to the electrostatic association of the negatively charged hyaloronate and the positively charged chitosan chains (FIG. 20b).

Figure 21:
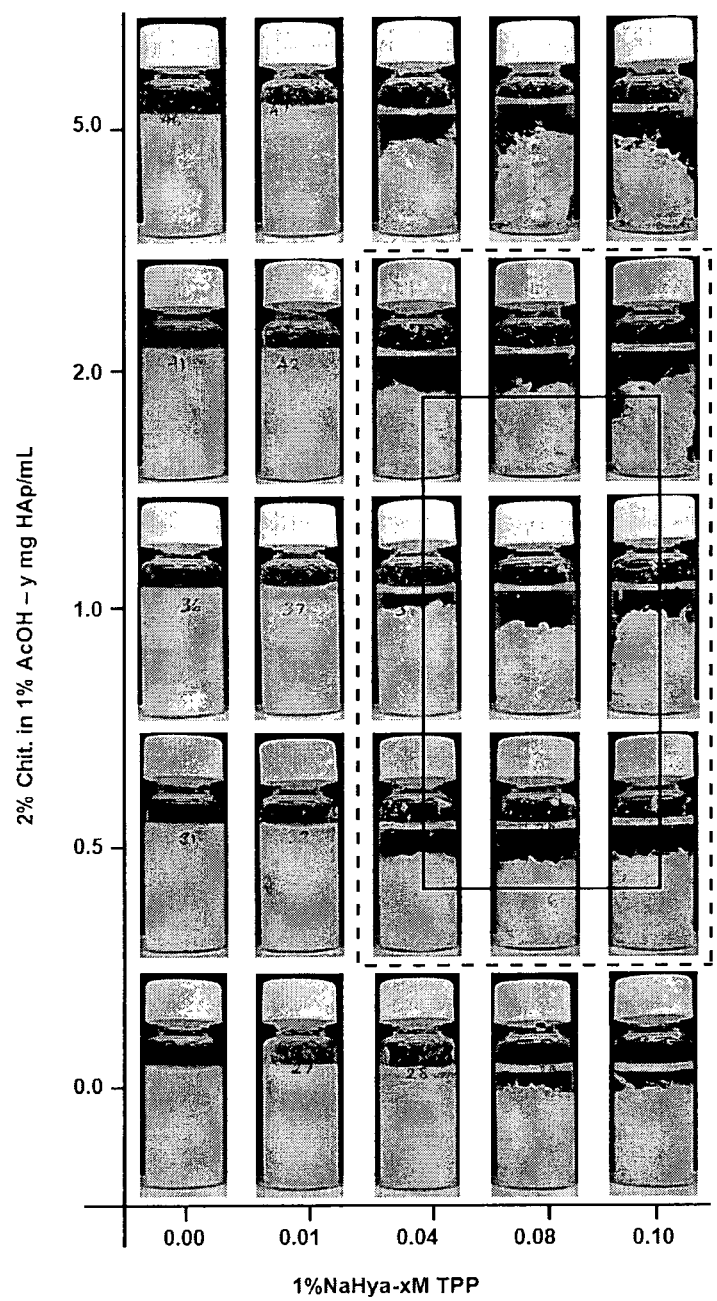
FIG. 21 A photographic representation of Chitosan (Chit)—Hydroxyapatite (HAp) concentration as a function of Sodium hyaluronate—TPP concentration. Gel compositions within the dashed lines represent the preferred compositions and those within the solid lines represent even more preferred compositions.

As seen previously, more intense colour of the products occurs at higher HAp levels. Composition range with NaHya indicating the region of preferred depot formation (see FIG. 21).

Example 7

Preferred Depot Composition by Colour Analysis, (Chit-HAp ChS-TPP)

Figure 22:
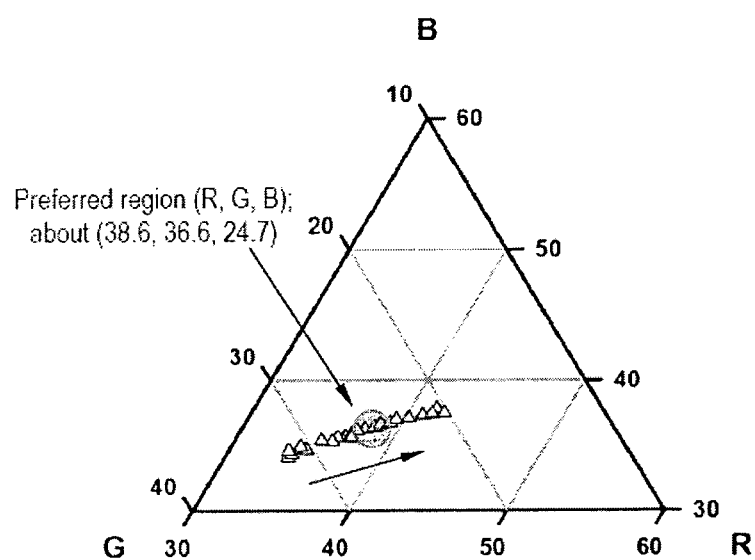
FIG. 22 Colour histogram representation. Arrow indicates increasing HAp and TPP in the depot forming composition.

The preferred depot composition can also be identified by colour histogram analysis, this is illustrated for the chitosan—hydroxyapatite—chrondroitin sulphate—TPP system (see FIG. 22). The mean value of each colour was considered. The values were normalized to 100% total, so that the intensity of the colour was disregarded.

Example 8

Gray Scale Histogram Analysis Indicating Preferred Regions of Depot Formation (Example Chit-HAp-ChS-TPP System)

Figure 23A:
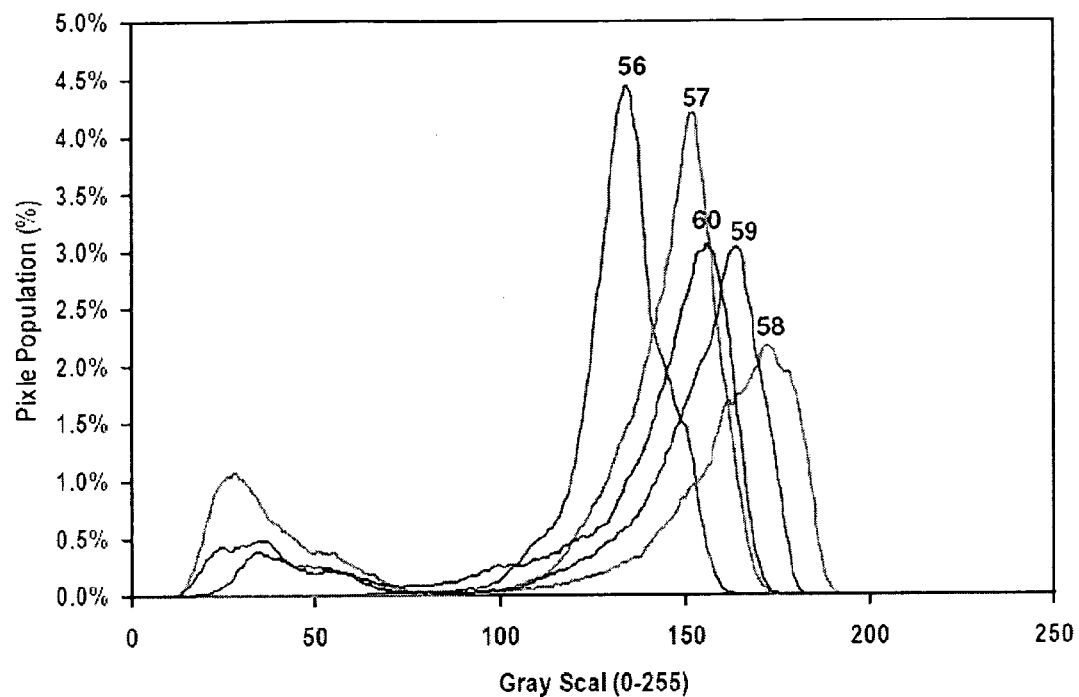
FIG. 23a Gray Scale histogram after 20 hours from depot maturing represented as Pixie population (%) as a function of Gray scale (0-255).
Figure 23B:
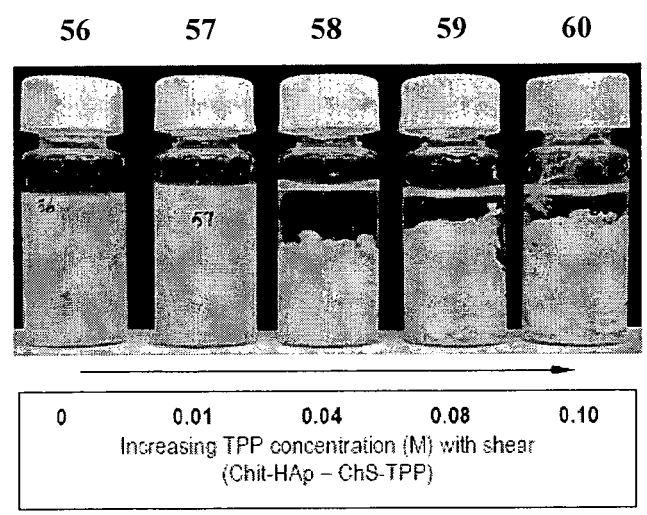
FIG. 23b A photographic representation of gel formation at increasing TPP concentration (M) with shear (Chit-HAp-ChS-TPP).

The transparency or opacity of the forming gel originates from two mechanisms; the first is the presence of HAp in the chitosan solution and the second is the phase separation of the polymers upon crosslinking with TPP or the aggregation of the positively charged chitosan and the negatively charged ChS, CMC or Hya. When these opposite charged polymers meet upon mixing they form a membrane at the interface of the two solutions or precipitate as a cloudy dispersion. These visual parameters are quantified as gray scale histograms (FIGS. 23a and 23b) when images of the system are taken on a black background.

Peaks at the low grey scale represent clear liquid since the black background is apparent and peaks at high values of the grey scale represent hydrogel or precipitate formation, while peak size quantifies the amount. Peak shape indicates the evolved microstructure of the depot hydrogel since it may be deconvoluted to provide texture information. Therefore, this grey scale technique quantifies the key parameters defining preferred formation compositions.

The Chit-HA-ChS-TPP systems outside region [vials 51, 52, 53, 54, 55] and within the preferred region [vials 61, 62, 63, 64, 65], resulting from compositions used in the synthesis (FIG. 23b) indicate the evolution of the hydrogel as well as its topographical microstructure. The development of this microstructure is indicated by the increasing complexity of the peak profile as shown by its deconvolution. Peaks in the lower values of the grey scale distribution (~50) indicate the supernatant liquid formed on phase separation, while peaks in the high values indicate depot formation. Complexity of the shape signifies increasing structural feature within the formed depot. With increasing TPP, phase separation is evident as well as an increasing peak complexity characteristic of greater structural texture in the preferred cross-linking degree [53, 54, 63, 64].

Figure 24:
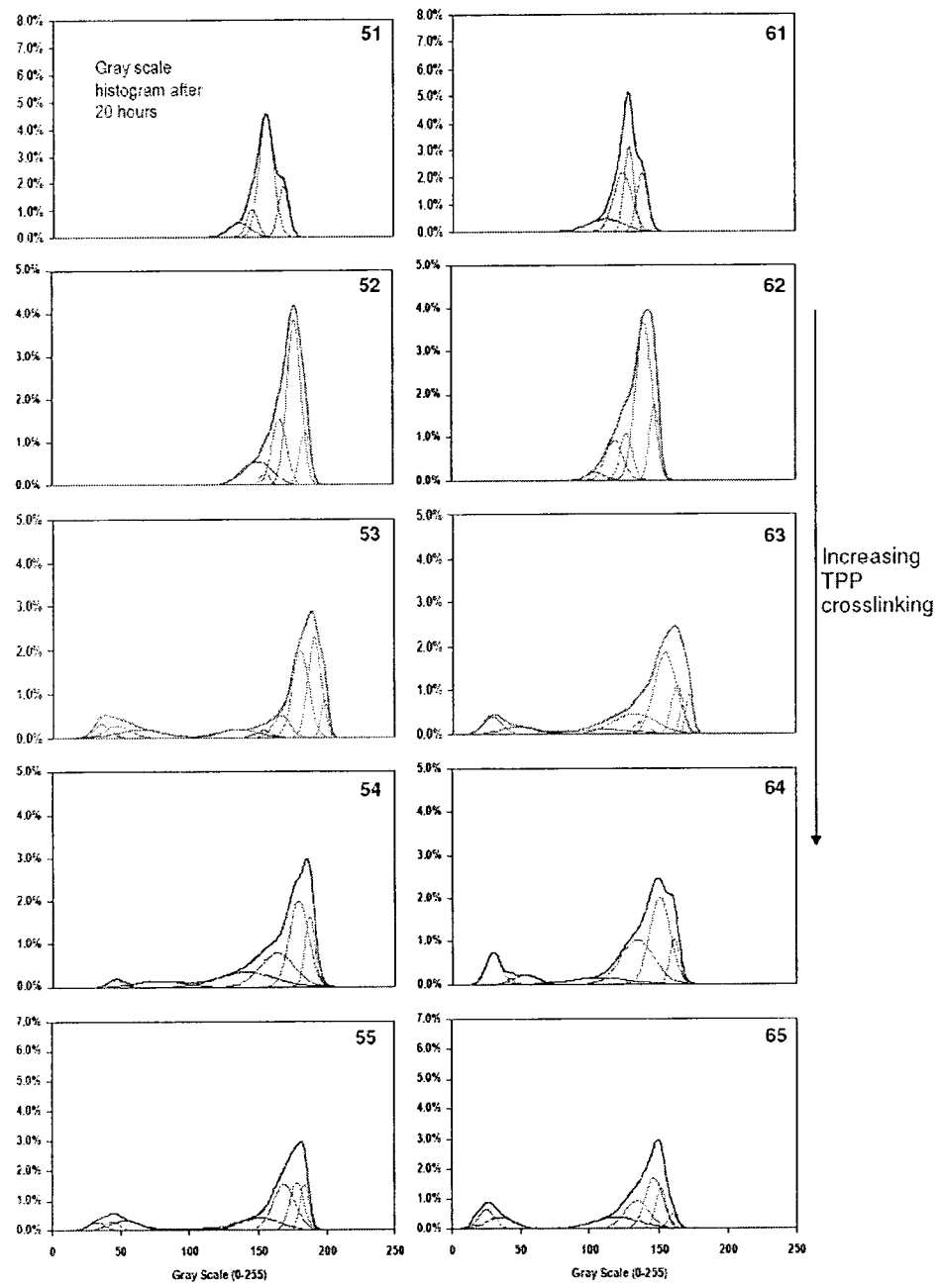
FIG. 24 Gray Scale histograms after 20 hours from depot maturing represented by Pixie population (%) as a function of Gray scale (0-255).

The Chit-HA-ChS-TPP systems both within the preferred compositional region and outside it show the evolution of the hydrogel as well as its topographical microstructure as indicated by the increasing complexity of the peak profile as shown by its deconvolution (FIG. 24).

Example 9

Production of Glucosamine Oligomers and Low Mw Chitosan for Conjugation with Proteins/peptides and Incorporation in the Depot (a) Heat Induced Hydrolysis Depolymerisation of Chitosan Chitosan was depolymerised under acidic HCl conditions (30 mL of 35% HCl was added to 30 mL of 2% chitosan in 1% AcOH) and heated using steam under a nitrogen blanket for 1 h. The mixture was neutralised using 40% NaOH in water. Ethanol was added to the mixture in an ice bath to precipitate all resultant chitosan.

The separated chitosan precipitate was resuspended in ethanol and centrifuged several times to complete purification to allow MW to be determined. The purified depolymerised chitosan precipitate was then freeze dried overnight; 0.35 g of dry chitosan mass was obtained representing an overall yield of 58%.

The reduced viscosity $\eta_{red}$ (or viscosity number $\eta_N$) was determined to obtain a molecular weight MW of the treated chitosan. Here, 150 mg of the heat treated chitosan was dissolved in 15 mL 0.2 M AcOH and 0.1 M AcONa to obtain 1% solution. Capillary viscometry (Type 531 10/I) at 25.00° C.±0.01 was used to obtain the limiting viscosity of 1 g/dL solutions with dilutions to 0.1 g/dL. The following expressions were used:

Specific viscosity:

$$\eta_{sp} = \frac{\eta}{\eta_0} - 1 \approx \frac{t}{t_0} - 1$$

Reduced viscosity or viscosity number ($\eta_N$):

$$\eta_{red} = \frac{\eta_{sp}}{c}$$

Limiting viscosity number or intrinsic viscosity:

$$[\eta] = \left(\frac{\eta_{sp}}{c}\right)_{c \to 0}$$

Figure 25:
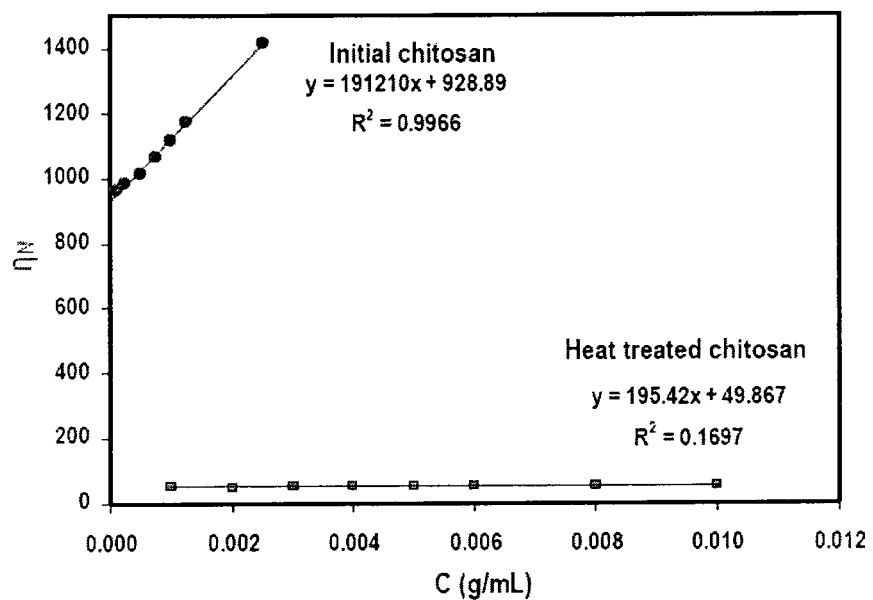
FIG. 25 Graph depicting viscosity number ($\eta_N$) as a function of C (mg/mL) for heat treated chitosan.

The intercept (see FIG. 25), [η], at C=0 for the treated chitosan is 49.867 applied to Staudinger's equation gives Mw of 60.113 kDa and (K=0.00083046 and α=0.9999 for DD=80%).

$[\eta]=KM^\alpha$

This gave a degree of polymerization 354 for the treated chitosan sample.

This reduced $M_w$ chitosan was able to produce particulate re-suspensible when neutralized with NaOH solution. A 0.25% solution of chitosan in 0.2 M AcOH and 0.1 M AcONa produced a cloudy suspension when mixed 4.4:1 (v/v) with 1N NaOH (pH=12.7), as seen in FIG. 26 (left).

Figure 26:
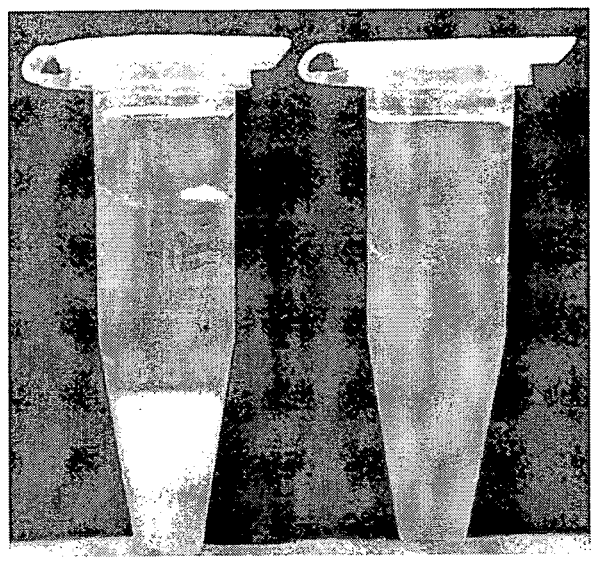
FIG. 26 Photographic representation of the particulate neutralised reduced Mw chitosan showing sedimentation—left and at resuspension—right.

The particulate in this suspension can be conjugated to polypeptides or proteins and dissolve by reducing the pH and mix with depot components for crosslinked attachment to the forming depot (see FIG. 26 (right)).

(b) Chitosan Depolymerisation Using Ultrasonication

Chitosan was depolymerised by ultrasonication where samples of 30 g of 2% chitosan in 0.2 M AcOH and 0.1 M sodium acetate (NaOAc) were ultrasonicated at varying temperatures and power inputs, using a 1 sec pulsed on/off program, as tabulated below.

Samples then were precipitated using 10% NaOH, centrifuged and washed with ethanol and then water several times until neutral pH were obtained, finally they were freeze dried. The samples were then characterised by GPC and intrinsic viscosity.

|   | Power | Mass | Temperature | Sonication Time | [η] (mL/g) | $M_w$ (kDa) |
|---|---|---|---|---|---|---|
| I | — | — | — | — | 928.89 | 1,120.1 |
| A | 50% | 30 g | 70° C. | 1 hour | 320.72 | 386.7 |
| B | 50% | 30 g | 85-90° C. | 1 hour | 291.95 | 352.0 |
| C | 90% | 30 g | 90° C. | 1 hour | 243.69 | 294.6 |

Figure 27:
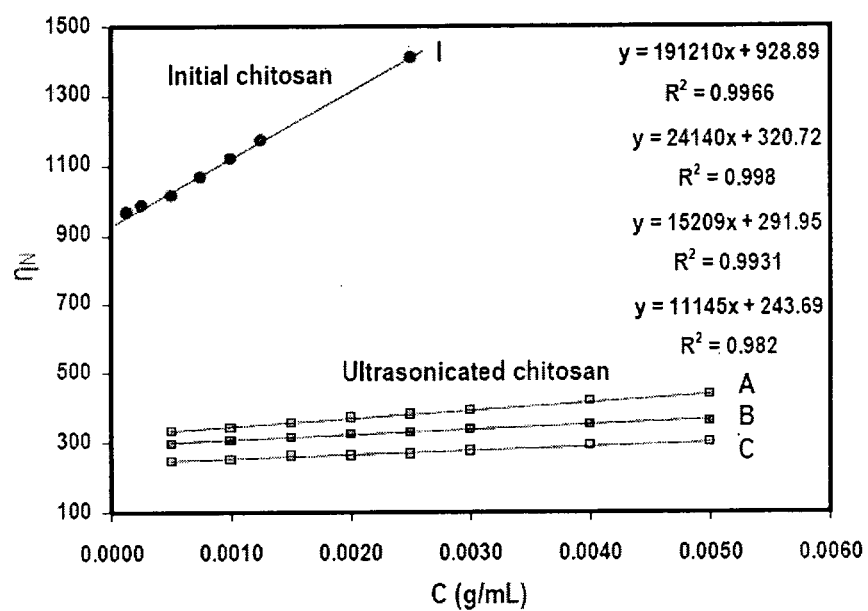
FIG. 27 Graph depicting viscosity number ($\eta_N$) as a function of C (mg/mL) for sonication treated chitosan.

FIG. 27 shows that ultrasonication reduced the initial chitosan (I) molecular weight from about $1.1 \times 10^6$ to as low as about $300 \times 10^3$ compared to acidified heating which yielded Mw of $60 \times 10^3$.

Example 10

Depot Formation and Vaccine Conjugation with Short Chain Chitosan (MW $60 \times 10^3$)

(a) Conjugation to Short Chain Chitosan

The amount of FITC or thiol-containing peptide in solution after conjugation to short chain chitosan was determined by:

Non-chloroacetylated (A) or chloroacetylated (B) short chain chitosan solutions were incubated with the fluorochrome FITC (32 µg/ml) (A) or a 3 kD thiol-containing peptide (2 mg/ml) (B). Solutions were adjusted to pH 8-9 with 1N NaOH and left to incubated overnight on a mixing rack at 37° C. The absorbance spectrum of each solution was measured at 0 hours and 24 hours later. FITC containing solutions were measured at a wavelength of 495 nm and peptide containing solutions at 280 nm.

Figure 28A:
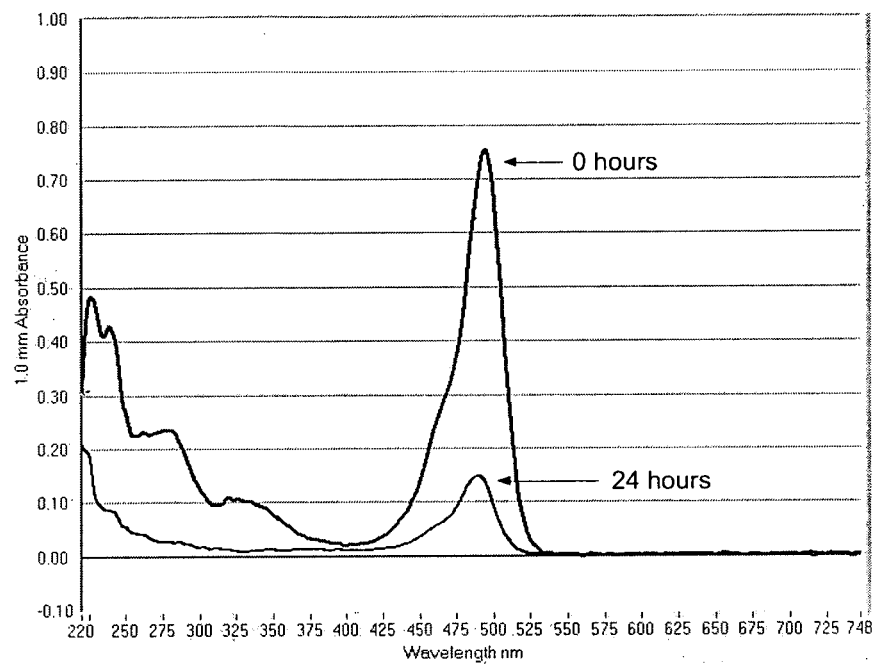
FIGS. 28a and 28b Graphs depicting UV-vis absorbance spectra of the supernatant of the reduced $M_w$ chitosan and chloroacetylated chitosan particulate suspension at the start and after 24 hours incubation with (a) FITC, and (b) polypeptide in the tagging and tethering reaction.

Initially the reactivity of the chitosan chain functional NH$_2$ groups was determined by conjugation of fluorescein isothiocyanate (FITC) and measurement of the FITC at 495 nm remaining in solution after conjugation for 24 hours. In FIG. 28a it can be seen that the majority of the FITC was covalently bound to the chitosan chains.

100 mg of the freeze dried short chain chitosan was suspended in 5 mL of dry acetone. 500 mg of chloroacetic acid and 50 mg of chloroactic anhydride was added to the tube and sealed. The mixture was stirred at 50° C. for 1 h to produce chloroacetylated short chain chitosan for polypeptide tethering.

Figure 28B:
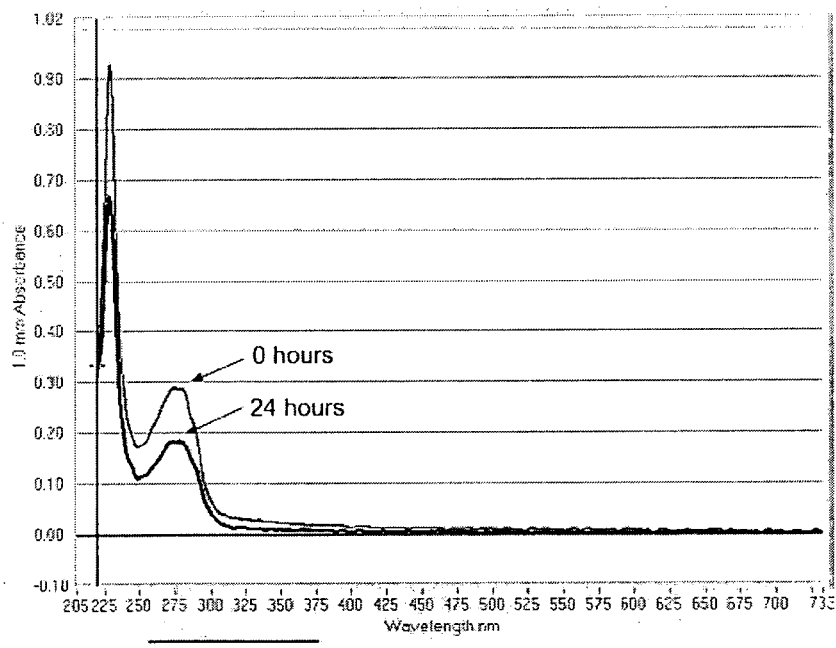

Thiol-containing peptide was then conjugated to chloroacetylated short chain chitosan by contact in solution for 24 hours, and the degree of peptide remaining in solution unconjugated was measured by the peptide intrisic fluorescence at 280 nm. Peptide binding is shown in FIG. 28b in terms of the solution fluorescence.

Figure 29A:
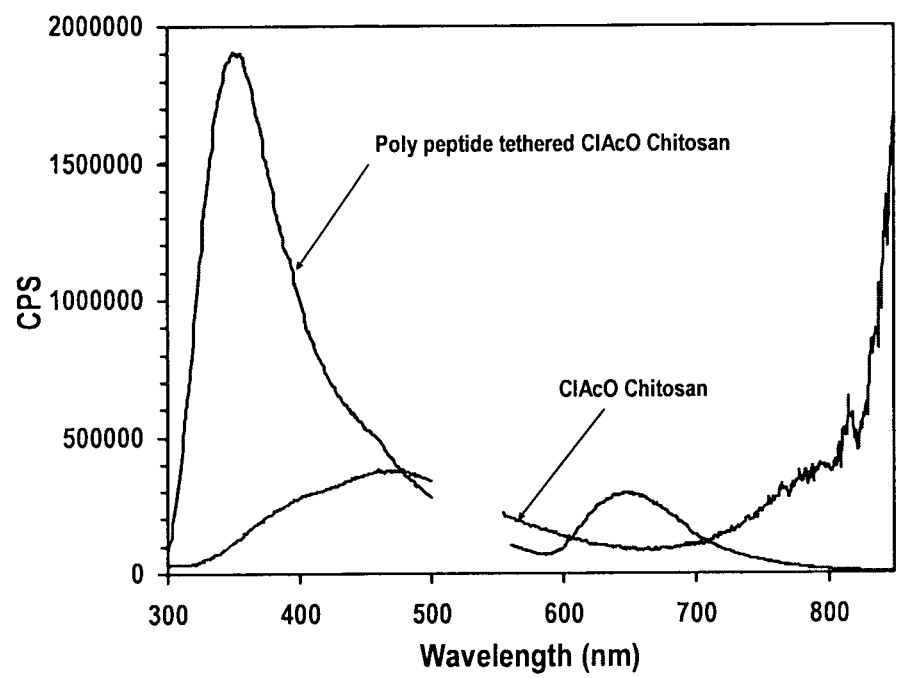
FIGS. 29a and 29b Graph depicting emission spectra of the freeze dried reduced $M_w$ chitosan and chloroacetylated chitosan and the polypeptide tethered and FITC tagged reduced $M_w$ chitosan.

The resulting peptide conjugated short chain chitosan was then analysed for the peptide content directly on solid dry samples and compared to the chloroacetylated (ClAcO) chitosan prior to conjugation by solid state fluorescence excited at 270 nm as shown in FIG. 29a.

Figure 29B:
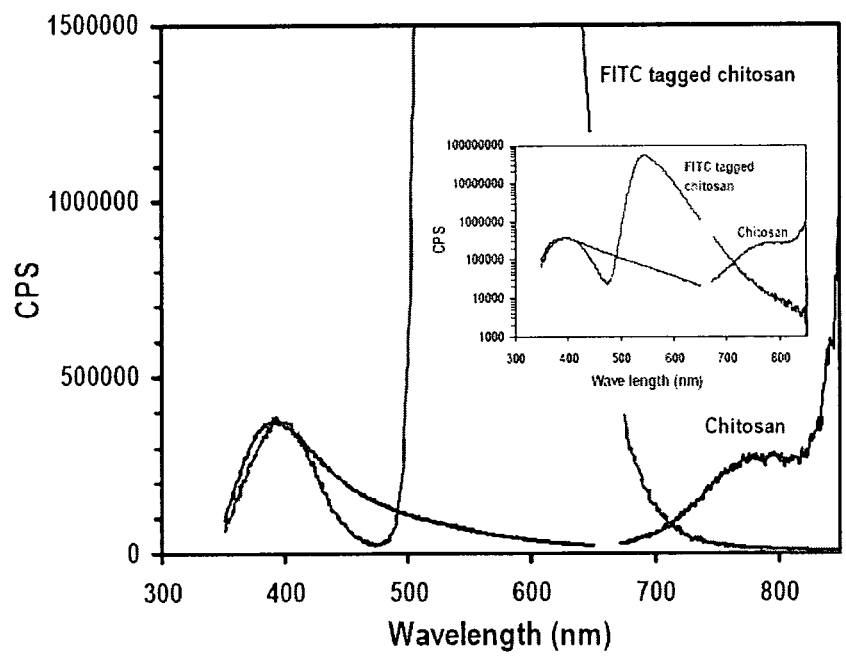

The amine functionality of the short chain chitosan was verified by FITC conjugation and fluorescence spectra excited at 330 nm, as shown in FIG. 29b.

Figure 30A:
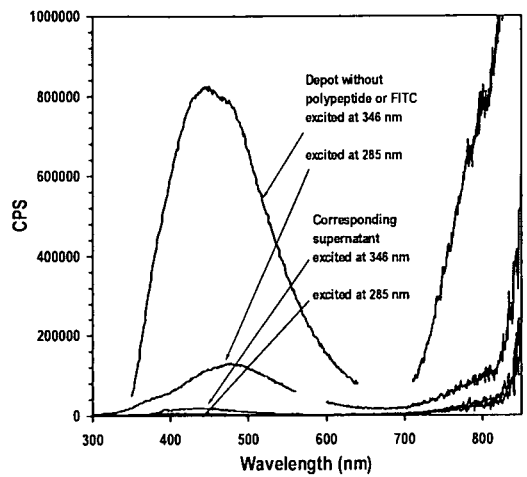
FIGS. 30a-30c Graph depicting emission spectra of FITC and polypeptide loaded depots and their corresponding supernatants.

(b) Incorporation of Short Chain Chitosan, FITC Tagged Short Chain Chitosan, and Polypeptide Conjugated Short Chain Chitosan into Depot Depot formation was achieved by the mixing of long chain polymeric chitosan as the major component with short chain chitosan which acted as a vector carrying a conjugated polypeptide into the structure of the depot. In this way polypeptide is covalently linked to the depot structure via the short chains while the mechanical properties of the depot are retained by the polymeric chitosan component. Intrinsic fluorescence of the depot and its supernatant excited at 285 nm (polypeptide) and 346 nm (FITC). FIG. 30a shows that all long chain polymeric chitosan is taken up in depot formation.

Figure 30B:
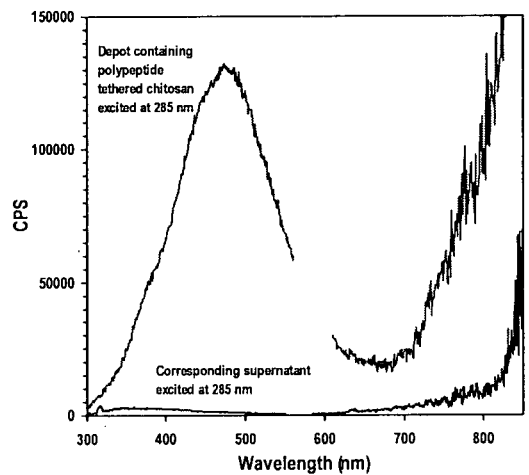

Depots were formulated by mixing solutions of polymeric chitosan with polypeptide tethered chitosan chains. FIG. 30b shows during formation of the depot all polypeptide tethered short chain chitosan is incorporated within the structure.

Figure 30C:
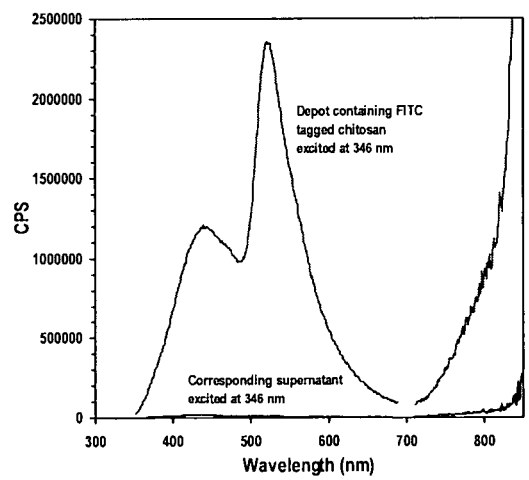

To establish that the short chitosan chains were incorporated into the depot, FITC tagged short chain chitosan was mixed with the polymeric chitosan forming the depot. FIG. 30c shows the emission spectra (excited at 346 nm) of the resultant depot and its supernatant show that FITC tagged short chains are totally incorporated.

Example 11

Syneresis Study (a) Antigen Uptake During Depot Formation and Release (Initial Quantity of Lysozyme Only)

Figure 31:
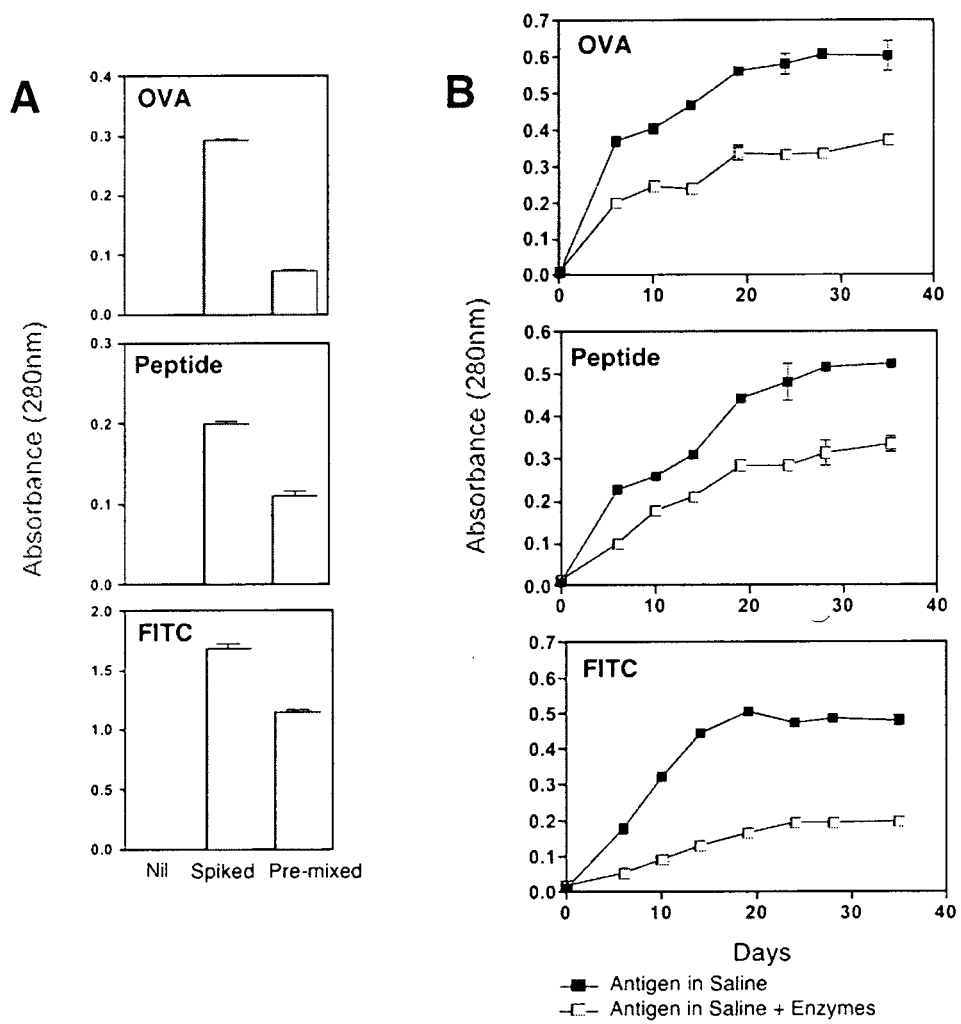
FIG. 31 Graphs and bar charts depicting absorbance (280 nm) as a function of time (days) for various peptides.

Antigen uptakes by depot formation (A) and release into supernatant under incubation (B) with initial physiological concentrations of human lysozyme and glucosaminidase are shown in FIG. 31.

100 µl of saline containing antigens (400 µg) in the form of the protein ovalbumin (OVA) a peptide antigen or a fluorochrome label (FITC) were premixed in 1 ml of chitosan solution. Depots were formed by adding the chitosan solution with (Pre-mixed) or without antigen (Nil) to 1 ml of tripolyphosphate solution and allowed to stand for 10 minutes before mixing vigorously. Absorbance readings (280 nm) of the supernatant after depot formation were then taken at various time points to determine the remaining amount of antigen left in solution. As a comparison, absorbance readings were also conducted on depot supernatants formed in the absence of antigen but deliberately spiked with the same amount of antigen used for the pre-mixed depot. (B) Antigen-containing depots were incubated in 500 µl saline in the absence or presence of the enzymes lysozyme (50 µg/ml) and N-acetyl-beta-D-glucosaminidase (10 U/L) at 37° C. Absorbance readings (280 nm) of the depot solutions were taken at various times points. Each symbol represents the average and standard error from triplicate absorbance readings (see FIG. 31).

(b) Antigen Uptake During Depot Formation and Release (Lysozyme Replenished)

Figure 32:
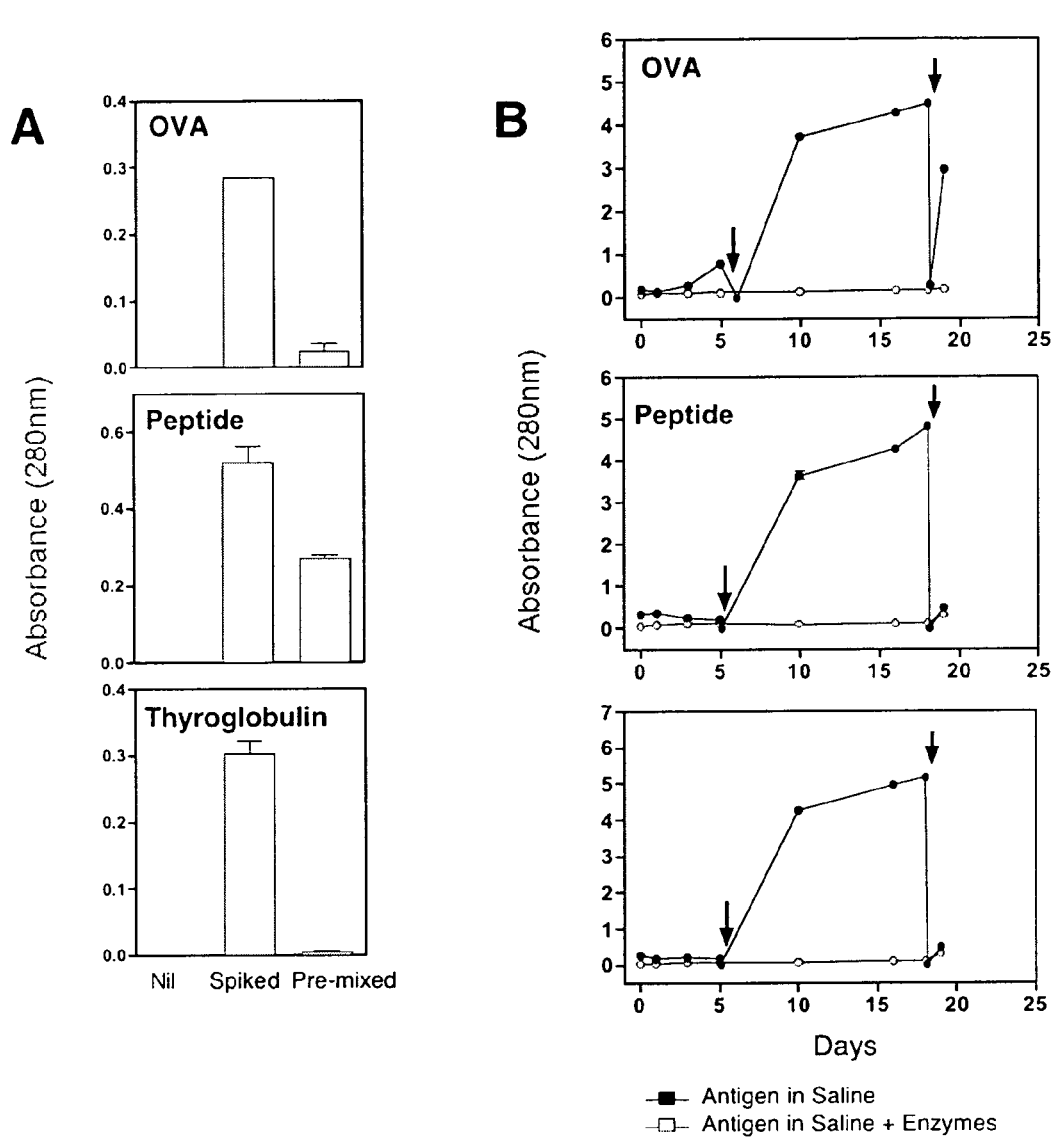
FIG. 32 Graphs and bar charts depicting absorbance (280 nm) as a function of time (days) for various peptides.

Antigen uptake by depot formation (A) and release into supernatant (B) under incubation with continually replenished chicken lysozyme is shown in FIG. 32.

(A) Depots were formed by mixing 100 µl of saline containing antigens (400 µg) in 1 ml of chitosan solution which was then added to 1 ml of tripolyphosphate solution. After the formation of the depot, absorbance readings at 280 nm were taken to determine the amount of antigen remaining in solution to establish verify antigen uptake as in the previous figure.

(B) Antigen-containing depots were incubated in 500 µl saline in the absence or presence of hen egg lysozyme (2 mg/ml) at 37° C. Absorbance readings (280 nm) of the depot solutions were taken at various times points. Enzyme solutions were replaced with fresh solutions on days 5 and 18 (as indicated by arrows, FIG. 32). Each symbol represents the average and standard error from triplicate absorbance readings.

(c) Vaccine Immune Response In-Vivo (Mice) with Depot

Figure 33:
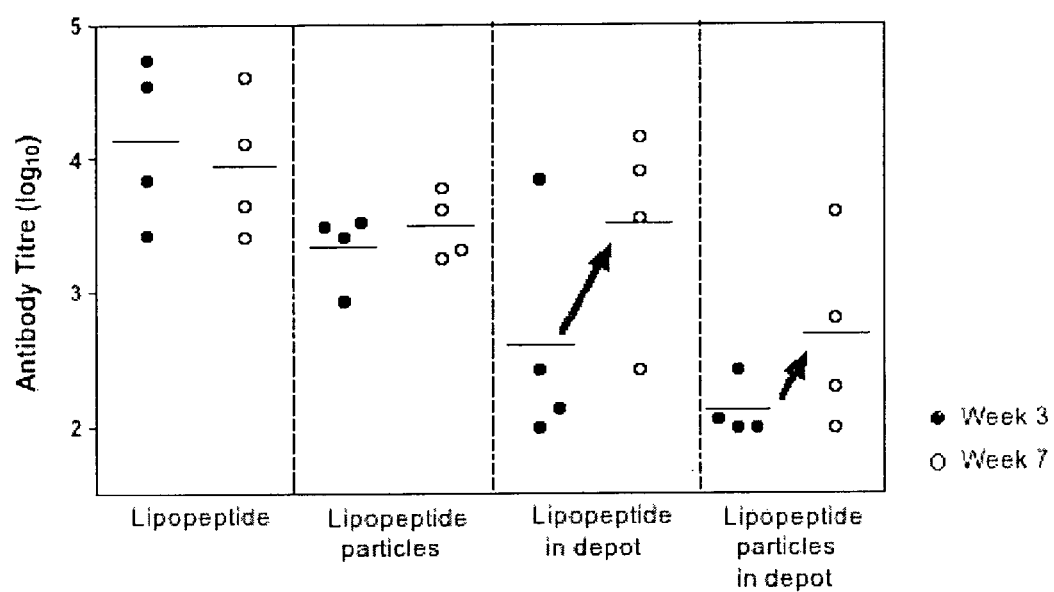
FIG. 33 Plot of antibody titre ($\log_{10}$) for various mice groups injected with various forms of lipopeptide. Antibody titres were assessed after 3 and 7 weeks.

Antibody response elicited by vaccination is shown in FIG. 33.

Mice (4 per group) were vaccinated at the scruff of the neck with 20 nmoles of free lipopeptide or lipopeptide-conjugated microparticles. Vaccinations were also carried out under anaesthetic using a dual injection needle system containing 20 nmoles of lipopeptide or lipopeptide-conjugated particles formulated with chitosan solution in one syringe and tripolyphosphate solution in the other. Mice were bled after 3 and 7 weeks to obtain sera and antibody titres were determined in an ELISA assay.

FIG. 33 indicates a high free antibody response consistent with a priming dose, and a lower but significant response to antigen within free particles that increases marginally from 3 to 7 weeks. Lipopeptide antibody within the Depot itself and within particles within the Depot show delay sufficiently significant to begin to elicit an immune response at week 7. The greater immobilization, that is antibodies within particles which are within the depot show the greatest delay (as indicated by the arrows).

The claims defining the invention are as follows:
1. A prolonged release and/or controlled release delivery system for delivery of a biologically active agent, the system comprising:
(i) a first component comprising a biocompatible polyaminosaccharide; and
(ii) a second component comprising a biocompatible phosphate or biocompatible sulphonamide compound capable of crosslinking with the first component, wherein the delivery system further comprises the biologically active agent, an aqueous insoluble alkaline earth metal phosphate, and a biocompatible glycan;

wherein each of the biologically active agent, aqueous insoluble earth metal phosphate and biocompatible glycan is present in either of the first and/or second components; and wherein the % wt/wt ratio ranges of:

the biocompatible polyaminosaccharide to the aqueous insoluble alkaline earth metal phosphate is from about 40:1 to about 10:1; and the biocompatible polyaminosaccharide to the biocompatible phosphate or biocompatible sulphonamide is from about 100:74 to about 100:184; and whereby the first and second components of the system are physically isolated and, when in use, combining of the first and second components promotes crosslinking and results in the formation of a biopolymer hybrid gel-depot including the biological active agent.

2. The delivery system according to claim 1 wherein the biocompatible polyaminosaccharide is chitosan or a salt thereof.

3. The delivery system according to claim 2 wherein the biologically active agent is conjugated to the chitosan.

4. The delivery system according to claim 1 wherein the biocompatible phosphate or sulphonamide is sodium triphosphate (TPP).

5. The delivery system according to claim 1 wherein the aqueous insoluble alkaline earth metal phosphate is hydroxyapatite.

6. The delivery system according to claim 1 wherein the biocompatible glycan is selected from chondroitin sulphate, sodium hyaluronate, and carboxymethyl cellulose.

7. The delivery system according to claim 1 wherein the biocompatible glycan is a proteoglycan.

8. The delivery system according to claim 1 wherein the biological active agent is selected from the group consisting of insulin, cortisol, estrogen or growth hormone, infliximab, adalimumab, nituximab, alemtuzumab, daclizumab, basiliximab etanercept and LHRH.

9. The delivery system according to claim 1 wherein the biopolymer hybrid gel-depot including the biological active agent has a Young's modulus in the range of about 20 to 60 kPa.

10. The delivery system according to claim 1 wherein the biopolymer hybrid gel-depot including the biological active agent has a compressive modulus in the range of about 100 kPa to 500 kPa.

11. A method of forming a prolonged release and/or controlled release biopolymer hybrid gel-depot including a biologically active agent, said method comprising:

(i) providing a first component comprising a biocompatible polyaminosaccharide, and a second component comprising a biocompatible phosphate and/or sulphonamide compound capable of crosslinking with the first component, (a) wherein the first and/or second component further comprises the biologically active agent; and (b) wherein the first and/or second component also comprises:

(i) an aqueous insoluble alkaline earth metal phosphate; and/or (ii) a biocompatible glycan and/or proteoglycan wherein the % wt/wt ratio ranges of:

the biocompatible polyaminosaccharide to the aqueous insoluble alkaline earth metal phosphate is from about 40:1 to about 10:1; and the biocompatible polyaminosaccharide to the biocompatible phosphate or biocompatible sulphonamide is from about 100:74 to about 100:184; and (ii) combining the first and second components for a time and under conditions to promote crosslinking and to form a biopolymer hybrid gel-depot including the biologically active agent.

12. A biopolymer hybrid gel-depot comprising:

(i) a biocompatible polyaminosaccharide;

(ii) a biocompatible phosphate and/or sulphonamide substantially crosslinked to (i);

(iii) an aqueous insoluble alkaline earth metal phosphate;

(iv) a biocompatible proteoglycan; and (v) a biologically active agent, wherein the % wt/wt ratio ranges of:

the biocompatible polyaminosaccharide to the aqueous insoluble alkaline earth metal phosphate is from about 40:1 to about 10:1; and the biocompatible polyaminosaccharide to the biocompatible phosphate or biocompatible sulphonamide is from about 100:74 to about 100:184.

13. A biopolymer hybrid gel-depot comprising:

(i) chitosan (or a suitably functionalised derivative thereof);

(ii) tripolyphosphate substantially crosslinked to (i);

(iii) hydroxyapatite;

(iv) chondroitin sulphate; and (v) a biologically active agent wherein the % wt/wt ratio ranges of:

the chitosan to the hydroxyapatite is from about 40:1 to about 10:1; and the chitosan to the tripolyphosphate is from about 100:74 to about 100:184.

14. A method of delivering a biologically active agent to a subject including the step of administering:

(i) a first component comprising a biocompatible polyaminosaccharide; and (ii) a second component comprising a biocompatible phosphate and/or sulphonamide compound capable of crosslinking with the first component, wherein (a) the first and/or second component further comprises the biologically active agent; and (b) the first and/or second compounds also comprises:

an aqueous insoluble alkaline earth metal phosphate; and/or (ii) a biocompatible glycan and/or proteoglycan;

wherein the % wt/wt ratio ranges of:

the biocompatible polyaminosaccharide to the aqueous insoluble alkaline earth metal phosphate is from about 40:1 to about 10:1; and the biocompatible polyaminosaccharide to the biocompatible phosphate and/or biocompatible sulphonamide is from about 100:74 to about 100:184; and whereby the first and second components are simultaneously or sequentially injected at the same site.

15. A method of delivering a biologically active agent to a subject including the step of implanting a biopolymer hybrid gel-depot comprising:

(i) a biocompatible polyaminosaccharide;

(ii) a biocompatible phosphate and/or sulphonamide substantially crosslinked to (i);

(iii) an aqueous insoluble alkaline earth metal phosphate;

(iv) a biocompatible glycan and/or proteoglycan; and
(v) a biologically active agent
wherein the % wt/wt ratio ranges of:
the biocompatible polyaminosaccharide to the aqueous insoluble alkaline earth metal phosphate is from about 40:1 to about 10:1; and
the biocompatible polyaminosaccharide to the biocompatible phosphate and/or biocompatible sulphonamide is from about 100:74 to about 100:184.

16. A prolonged release and/or controlled release delivery system for delivery of a biologically active agent, the system comprising:
(i) a first component comprising a biocompatible polyaminosaccharide, the biologically active agent, and an aqueous insoluble alkaline earth metal phosphate; and
(ii) a second component comprising a biocompatible phosphate or biocompatible sulphonamide compound capable of crosslinking with the first component, and a biocompatible glycan;
wherein the % wt/wt ratio ranges of:
the biocompatible polyaminosaccharide to the aqueous insoluble alkaline earth metal phosphate is from about 40:1 to about 10:1; and
the biocompatible polyaminosaccharide to the biocompatible phosphate or biocompatible sulphonamide is from about 100:74 to about 100:184; and
whereby the first and second components of the system are physically isolated and, when in use, combining of the first and second components promotes crosslinking and results in the formation of a biopolymer hybrid gel-depot including the biological active agent.

17. A prolonged release and/or controlled release delivery system for delivery of a biologically active agent to a subject, the system comprising:
(i) a first component comprising a biocompatible polyaminosaccharide; and
(ii) a second component comprising a biocompatible phosphate or biocompatible sulphonamide compound capable of crosslinking with the first component;
wherein the delivery system further comprises the biologically active agent, an aqueous insoluble alkaline earth metal phosphate and a biocompatible glycan;
wherein each of the biologically active agent, aqueous insoluble earth metal phosphate and biocompatible glycan is present in either of the first and/or second components; and
wherein the % wt/wt ratio range of:
the biocompatible polyaminosaccharide to the aqueous insoluble alkaline earth metal phosphate is from about 40:1 to about 10:1; and
the biocompatible polyaminosaccharide to the biocompatible phosphate or biocompatible sulphonamide is from about 100:74 to about 100:184; and
whereby the first and second components of the system are physically isolated and, when injected into the subject result in the formation of a biopolymer hybrid gel-depot including the biological active agent in the subject, wherein the biopolymer hybrid gel-depot including the biological active agent has a compressive modulus in the range of about 100 kPa to 500 kPa.

18. The delivery system according to claim 17, wherein the biocompatible polyaminosaccharide is chitosan or a salt thereof.

19. The delivery system according to claim 17, wherein the biologically active agent is conjugated to the chitosan.

20. The delivery system according to claim 17, wherein the biocompatible phosphate or biocompatible sulphonamide is sodium triphosphate (TPP).

21. The delivery system according to claim 17, wherein the insoluble alkaline earth metal phosphate is hydroxyapatite.

22. The delivery system according to claim 17, wherein the biocompatible glycan is selected from the group consisting of chondroitin sulphate, sodium hyaluronate, and carboxymethyl cellulose.

23. The delivery system according to claim 22, wherein the biocompatible glycan is chondroitin sulphate.

24. The delivery system according to claim 17, wherein the biopolymer hybrid gel-depot including the biological active agent has a Young's modulus in the range of about 20 to 60 kPa.

* * * * *